US009872706B1

United States Patent
Mullaney et al.

(10) Patent No.: US 9,872,706 B1
(45) Date of Patent: Jan. 23, 2018

(54) EXTERNAL FIXATION DEVICE

(71) Applicant: Devise Ortho Inc., Germantown, TN (US)

(72) Inventors: Michael W. Mullaney, Naples, FL (US); Stephen T. Miller, Scotts Valley, CA (US); William B. Austin, Germantown, TN (US); Todd A. Martens, Denver, CO (US)

(73) Assignee: Devise Ortho Inc., Germantown, TN (US)

( * ) Notice: Subject to any disclaimer, the term of this patent is extended or adjusted under 35 U.S.C. 154(b) by 41 days.

(21) Appl. No.: 14/712,471

(22) Filed: May 14, 2015

Related U.S. Application Data

(60) Provisional application No. 61/992,964, filed on May 14, 2014.

(51) Int. Cl.
*A61B 17/64* (2006.01)
*A61B 17/66* (2006.01)

(52) U.S. Cl.
CPC .......... *A61B 17/6475* (2013.01); *A61B 17/66* (2013.01)

(58) Field of Classification Search
CPC . A61B 17/64; A61B 17/6458; A61B 17/6466; A61B 17/6475; A61B 17/6483; A61B 17/66
See application file for complete search history.

(56) References Cited

U.S. PATENT DOCUMENTS

| | | | | | |
|---|---|---|---|---|---|
| 5,160,335 | A | * | 11/1992 | Wagenknecht | .... A61B 17/6466 606/57 |
| 5,207,676 | A | * | 5/1993 | Canadell | ............ A61B 17/6491 606/54 |
| 5,601,551 | A | * | 2/1997 | Taylor | .................... A61B 17/66 606/53 |
| 6,409,729 | B1 | * | 6/2002 | Martinelli | .......... A61B 17/6466 606/59 |
| 2013/0296857 | A1 | * | 11/2013 | Barnett | ............. A61B 17/6416 606/57 |
| 2014/0257288 | A1 | * | 9/2014 | Chang | ................ A61B 17/6466 606/59 |

* cited by examiner

*Primary Examiner* — Julianna N Harvey
(74) *Attorney, Agent, or Firm* — Haynes and Boone, LLP

(57) ABSTRACT

An external fixation system for the correction of long bone deformities includes an elongate beam element having an engagement feature along a longitudinal edge of the elongate beam element, a connector element secured to the elongate beam and structurally configured to support a first bone anchor extending from the external fixation system, and a movable carriage engaged with the engagement feature along the longitudinal edge of the elongate beam element and selectively movable along the engagement feature of the elongate beam element. The movable carriage is selectively lockable into a position along the elongate beam element. The movable carriage is structurally configured to support a second bone anchor extending from the external fixation system.

56 Claims, 23 Drawing Sheets

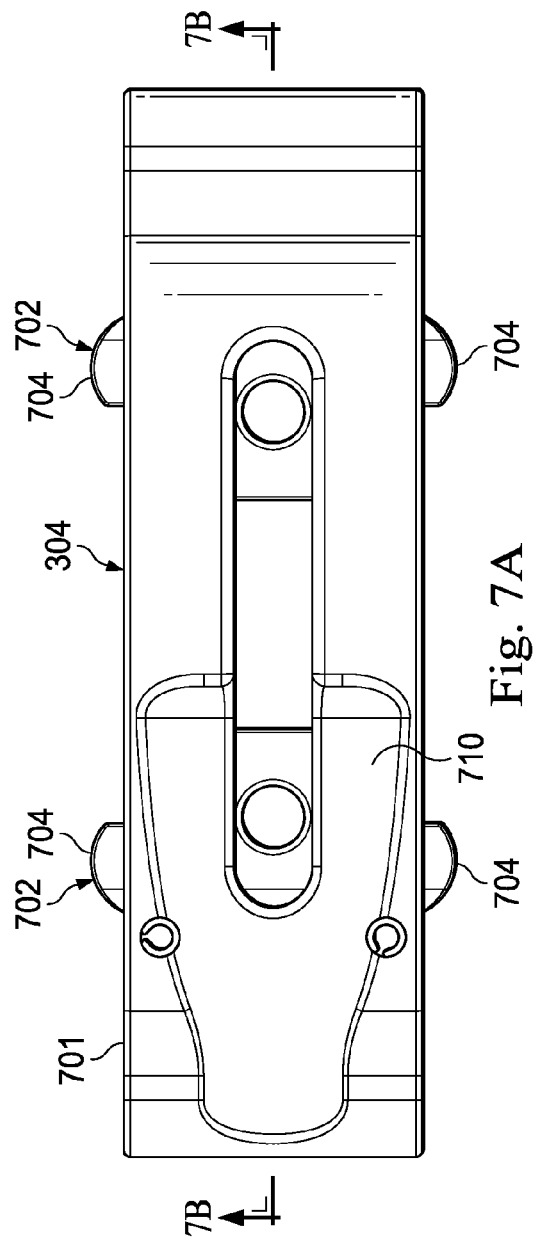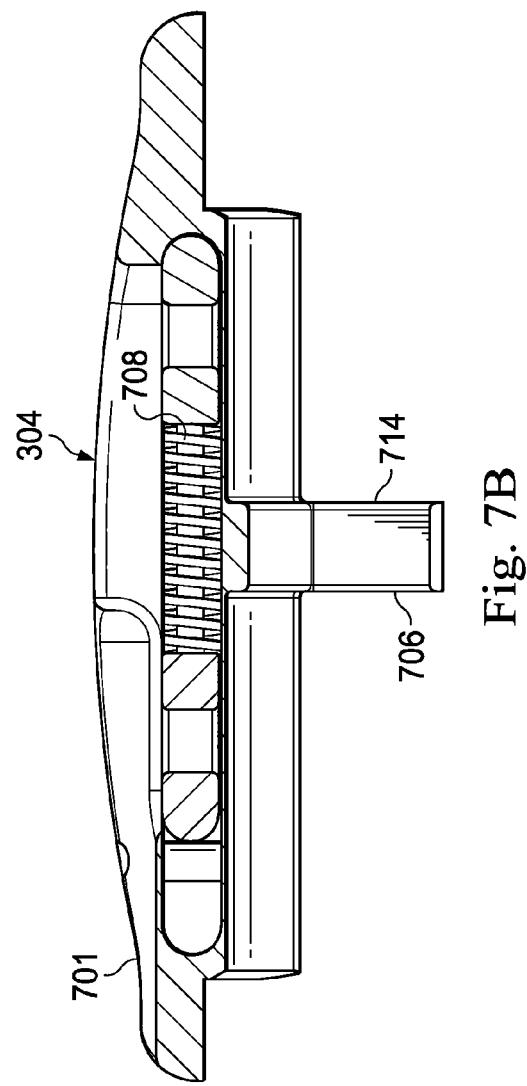
Fig. 7A
Fig. 7B

EXTERNAL FIXATION DEVICE

PRIORITY DATA

This application claims priority to Provisional Patent Application No. 61/992,964, filed May 14, 2014, and entitled "Modular Rail Based External Fixation for Skeletal Deformity Correction," the disclosure of which is hereby incorporated by reference in its entirety.

FIELD OF THE INVENTION

This application relates to systems that aid in the correction of long bone deformities of the skeletal system including limb lengthening.

BACKGROUND

Many systems exist on the market today to address long bone deformities. They include ring based systems such as the Ilizarov type fixation which can be built to suit the particular deformity being addressed, spatial frame type fixators that utilize software and a 6 degree of freedom (6-DOF) capability to address a very broad range of deformities without a built to suit configuration, and several linear based systems that have varying degrees of mobility that can be built to suit, with limitation, the deformity being addressed. Generally, the linear based systems are the easiest to apply and to adjust throughout the correction process and they also do not require software. However, unlike the software driven 6-DOF spatial frames, these devices, at times throughout the correction process, may have to be reconfigured to address changes that occur due to the changes to the bone from being partially corrected.

All linear systems utilize bone pins or bone anchors otherwise known as half pins anchored in groups to each of the bone segments in need of manipulation. Individual components, referred to as clamps or anchor blocks, are then attached to each of the bone anchor groups. These components act to structurally link the pins within each group together and provide an interface to the greater structure at large. One type of linear structural element, typically referred to as a rail, can then be attached to the clamp interface associated with each bone segment linking the segments together completing the overall structure. In most existing systems, these rails are available in multiple lengths to suit the particular condition. In some systems, these rails can be connected together to create a variety of lengths, however, in such systems, these connections often become a weak area and at times can be difficult to traverse with a traveling clamp. The clamps themselves are either locked to the rail or are free to travel along the rail. To affect such motion along the rail, elongate-able struts are used. Usually these come in the form of threaded rods and nuts whereby the nut is affixed to one clamp while the rod is affixed to the other. Rotation of the rod within the nut causes the two connected clamps to move relative to one another along the length of the rail. In all such systems the rail provides alignment and resistance to bending and torsional moments but does not provide any load support along the long axis of the rail, leaving that function to the elongate-able strut.

What is desired is an easy-to-apply linear based system that is modular and easily reconfigurable such that these changes can be made without having an exceedingly complex device configuration. The devices, systems, and methods disclosed herein address one or more of the shortcomings of the conventional system.

SUMMARY

An external fixation system for the correction of long bone deformities includes an elongate beam element having an engagement feature along a longitudinal edge of the elongate beam element, a connector element secured to the elongate beam and structurally configured to support a first bone anchor extending from the external fixation system, and a movable carriage engaged with the engagement feature along the longitudinal edge of the elongate beam element and selectively movable along the engagement feature of the elongate beam element. The movable carriage is selectively lockable into a position along the elongate beam element. The movable carriage is structurally configured to support a second bone anchor extending from the external fixation system.

An external fixation system for the correction of long bone deformities includes a movable carriage structurally configured to support a bone anchor extending from the external fixation system. The movable carriage includes a drive system having a rotatable element engagable with an engagement feature of an elongate beam element in a manner that rotation of the rotatable element advances the movable carriage along the elongate beam element and a selectively actuatable lock system to fix the movable carriage in a position along the elongate beam element.

An external fixation system for the correction of long bone deformities includes an elongate beam element having an engagement feature along a longitudinal edge of the elongate beam element, a connector element secured to the elongate beam and structurally configured to support a first bone anchor extending from the external fixation system, and a movable carriage engaged with the engagement feature along the longitudinal edge of the elongate beam element and selectively movable along the engagement feature of the elongate beam element. The movable carriage is selectively lockable into a position along the elongate beam element. The movable carriage is structurally configured to support a second bone anchor extending from the external fixation system. The fixation system further includes a supplementary beam element configured to fixedly attach to an end of the elongate beam element.

An external fixation system for the correction of long bone deformities includes a primary beam element and a secondary beam element. Each of the primary and secondary beam elements includes an engagement feature along a longitudinal edge thereof. The primary and secondary beam elements are securable to each other so that the engagement features of both the primary and secondary beam elements form a continuous engagement feature across the primary and secondary beam elements when secured to each other. The system further includes a carriage element connectable to the primary and secondary beam elements and comprising a drive system configured to engage with the continuous engagement feature and move the carriage element along the primary and secondary beam elements. The carriage element is structurally configured to support a bone anchor extending from the external fixation system.

Additional embodiments include connections between the rail segments and the anchor blocks that allow for adjustment of the angle between the anchor blocks and the beam elements. Some embodiments incorporate a turntable on the moving carriage or fixed connector. Other embodiments include a hinge incorporated in the anchor block. Additional embodiments include a hinge element that connects two beam elements to allow the frame to span a joint and allow for joint function. Some embodiments include a hinge element or a family of hinge elements whose mounting can be adjusted such that a full range of hinge axis locations can be achieved. These hinge elements may benefit by having the same interface as the rail connection. With a similar interface added to the anchor blocks themselves, a high degree of flexibility can be achieved.

BRIEF DESCRIPTION OF THE DRAWINGS

The accompanying drawings illustrate embodiments of the devices and methods disclosed herein and together with the description, serve to explain the principles of the present disclosure.

FIGS. 7A, 7B, and 7C are diagrams showing an illustrative lock element according to one example constructed according to principles described herein.

DETAILED DESCRIPTION OF THE DRAWINGS

Figure 1:
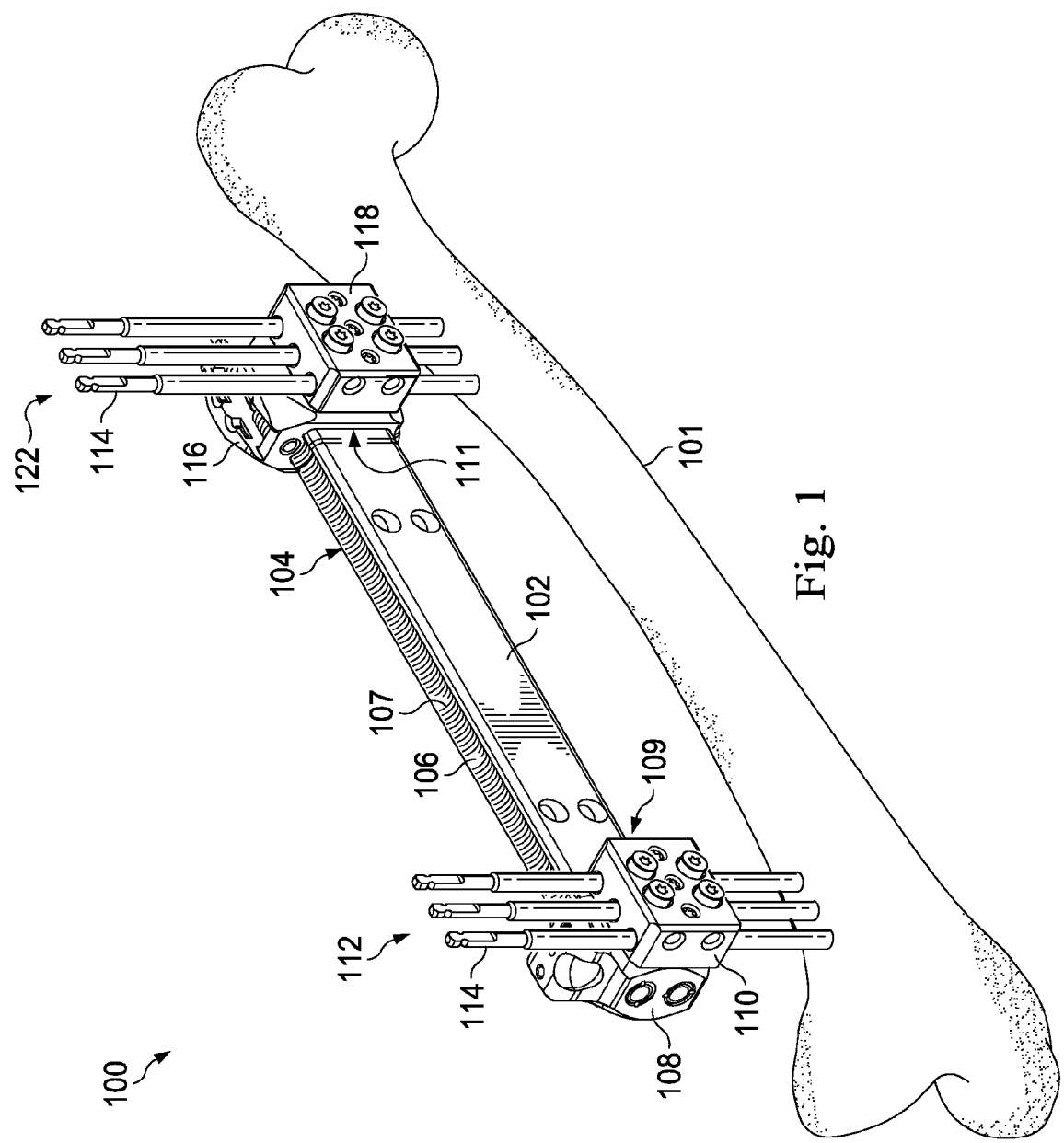
FIG. 1 is a diagram showing an illustrative fixation system attached to a bone according to one example constructed according to principles described herein.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure.

FIG. 1 is a diagram showing an illustrative fixation system 100 attached to a bone 101. For purposes of discussion, the bone 101 is shown in an intact, un-deformed state. According to the present example, the fixation system 100 includes an elongate beam element 102, a fixed connector element 108 positioned at an end 109 of the elongate beam element 102, and a movable carriage 116 secured to the elongate beam element 102.

The elongate beam element 102 is made of a sturdy material such as metal or a composite material. In the present example, the elongate beam element 102 has a substantially rectangular cross-section perpendicular to the longitudinal axis of the elongate beam element 102. In some examples, the elongate beam element 102 is substantially solid. In other examples, however, the elongate beam element 102 may have a hollow interior to allow for a lighter weight beam element. The hollow interior can be designed such that the elongate beam element 102 maintains sufficient strength.

The elongate beam element 102 includes an engagement feature 106 along a longitudinal edge 104 of the elongate beam element 102. In the present example, the engagement feature 106 includes a concave portion along the length of the elongate beam element 102. The engagement feature 106 may include a set of engagement elements 107. In some examples, the engagement elements 107 include a straight set of teeth. In some examples, however, the engagements elements 107 include helical threads. The engagement feature 106 is designed to engage with a drive system of the movable carriage 116. The drive system will be described in further detail below.

The movable carriage 116 is designed to securely attach to and move along a portion of the length of the elongate beam element 102. In the present example, the movable carriage 116 includes an opening 111 that is sized and shaped to allow the elongate beam element 102 to pass therethrough. The movable carriage 116 includes a drive system (described below) that is configured to move the movable carriage 116 along the elongate beam element 102 and lock the movable carriage 116 into a set position selectively preventing additional movement.

The movable carriage 116 is attached to an anchor block 118. As will be described in further detail below, the anchor block 118 may be connected to the movable carriage 116 via a turntable, a hinged element, some other adjustable connector, some other inadjustable connector, or more than one of these. The anchor block 118 is designed to hold an anchor set 122 of bone anchors 114 such as bone pins, bone screws, or bone bolts. The bone anchors 114 are designed to engage with the bone 101.

The fixed connector element 108 is similar to the movable carriage 116 except that the fixed connector element 108 does not move along the elongate beam element 102. In one example, the fixed connector element 108 is designed to securely and immovably engage with the engagement feature 106 of the elongate beam element 102. In some examples, as illustrated in FIG. 1, the fixed connector element 108 is secured to the end 109 of the elongate beam element 102.

The fixed connector element 108 is also attached to an anchor block 110. Depending on the embodiment, the anchor block 110 may also be connected to the fixed connector element 108 via a turntable, hinged element, or both. The anchor block 110 is designed to hold a different anchor set 112 of bone anchors 114.

Because the position of the movable carriage 116 is adjustable, the second set 122 of bone anchors 114 is movable with respect to the first set 112 of bone anchors 114. Thus, while the bone anchors 114 from both sets 112, 122 are anchored into the bone 101, the movable carriage 116 can be adjusted to move the bone anchors 114 and correct various bone deficiencies and/or perform various bone lengthening operations.

Figure 2:
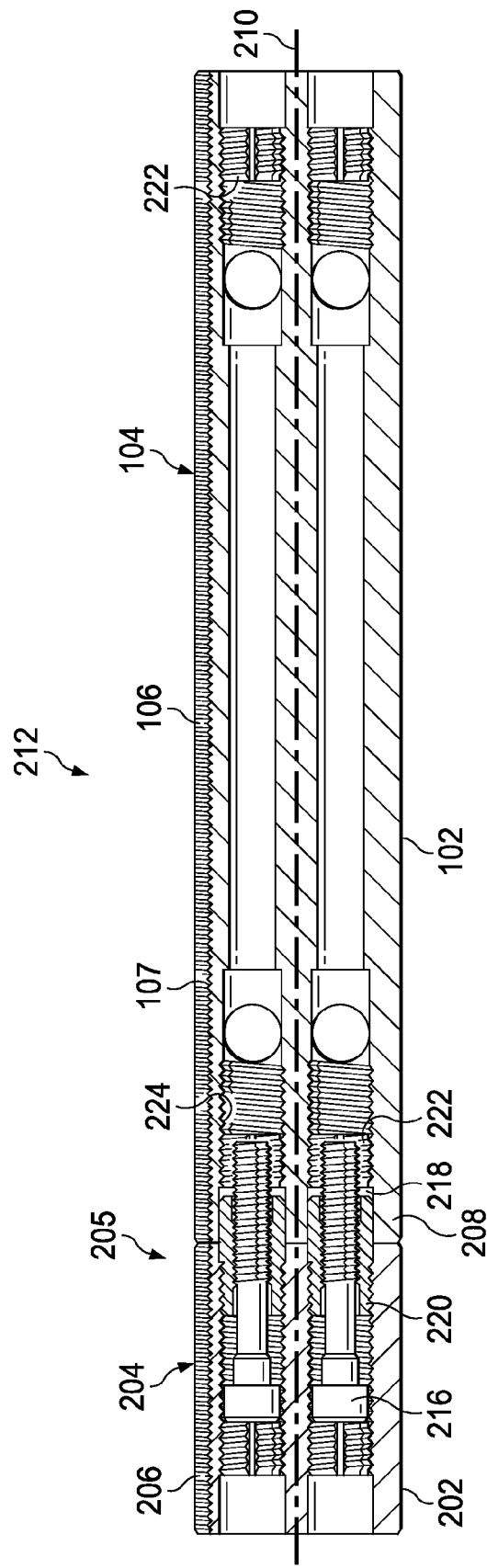
FIG. 2 is diagram showing an illustrative set of beam elements according to one example constructed according to principles described herein.

FIG. 2 is diagram showing an illustrative beam set 212 of beam elements 102, 202. The set 212 includes the elongate beam element 102 and a supplementary beam element 202. In some cases, the elongate beam element 102 may be referred to as the primary beam element and the supplementary beam element 202 may be referred to as the secondary beam element. In some cases, during a bone procedure, it may be desirable to extend the movable carriage beyond the length of the original elongate beam element 102. According to principles described herein, a supplementary beam element 202 that matches the elongate beam element 102 is secured to an end 208 of the elongate beam element 102. In other words, the cross-sectional shape of the supplementary beam element 202 that is perpendicular to longitudinal axis 210 is substantially similar to the corresponding cross-sectional shape of the elongate beam element 102.

The supplementary beam element 202 includes an engagement feature 206 along the longitudinal edge 204 of the supplementary beam element 202. The engagement feature 206 matches the engagement feature 106 of the elongate beam element 102. Thus, when the supplementary beam element 202 is secured to the elongate beam element 102, there is a single continuous engagement feature 205 that spans both beam elements 102, 202.

In one example, the supplementary beam element 202 is connected to the elongate beam element 102 via a set of threaded fasteners 216. In the present example, both beam elements 102, 202 include two through-holes 218 running the length of the beam elements 102, 202, and spaced away on either side of a centerline represented by axis 210. At the end of each of these through-holes 218 is a machined thread 224 that serves to accept either a threaded bushing 220 or a threaded insert 222. On the side with the threaded insert 222 there is also a counter-bore. The threaded bushing 220 on one of the beam elements aligns with and is inserted within the counter-bore of the other. A threaded fastener 216 aligned within the through-holes 218 captured between the threaded insert 222 and threaded bushing 220 is inserted through the threaded bushing 220 and into the threaded inserts 222 within the adjoined beam element. The head of the threaded fastener 216 bears upon the inside face of the threaded bushing 220. The tensile load in the threaded fastener 216 therefore draws the end faces of the adjoined beam elements together under load. The beam elements 102, 202 are primarily subjected to bending due to the offset loading. The substantially rectangular beam section is so positioned to maximize the beam element's moment of inertia by subjecting the width of the beam element rather than the thickness of the beam element to the greatest bending moment. By spacing the through-holes 218 and thus the threaded fasteners 216 as far away from the centerlines of the beam as practicable, the contribution in terms of tensile capability and compressive preload generated is maximized, giving the connection between the beam elements 102, 202 high strength and resistance to separation.

Figure 3:
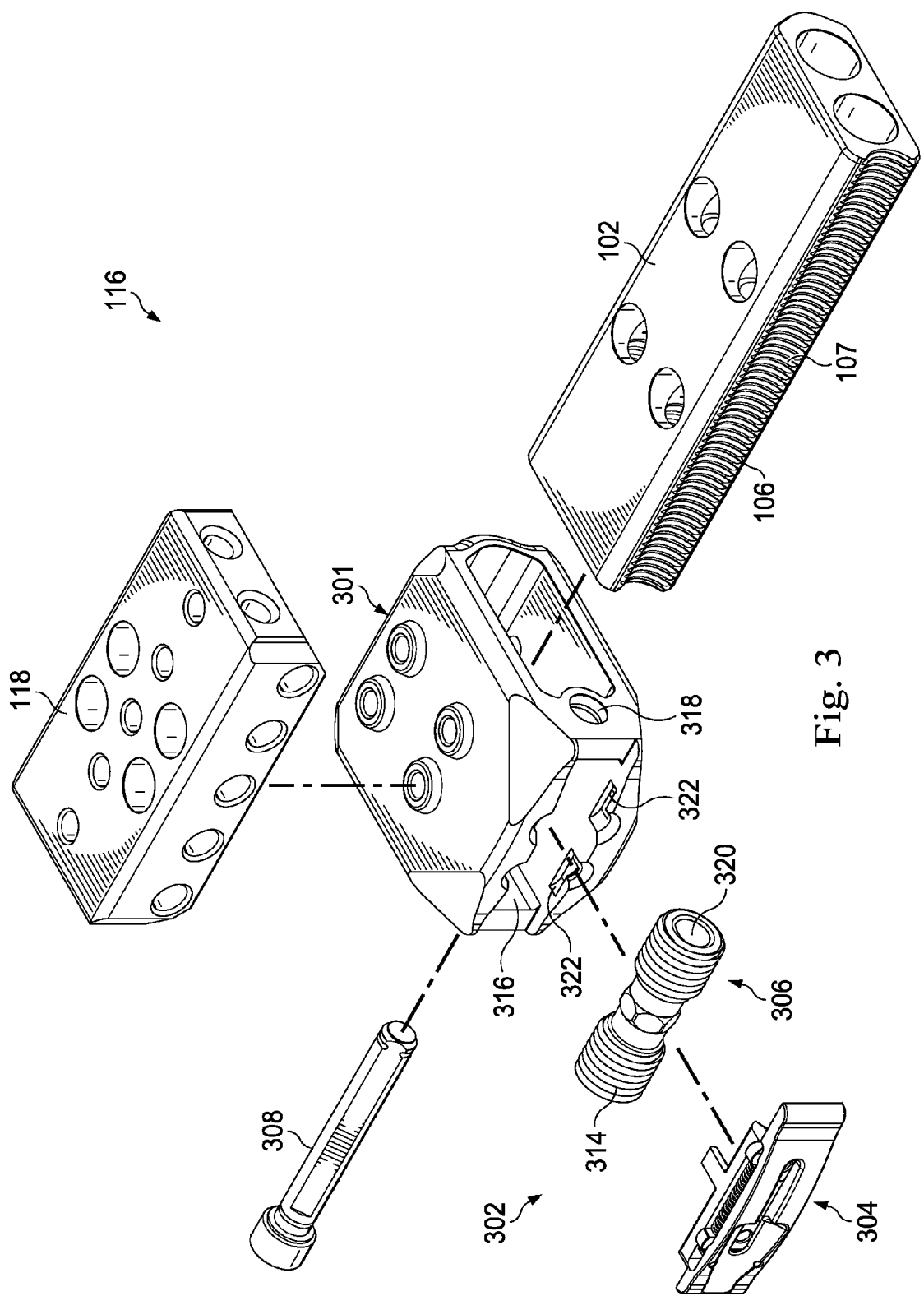
FIG. 3 is a diagram showing an exploded view of components of a movable carriage on a beam element configured to engage beam elements according to one example constructed according to principles described herein.

FIG. 3 is a diagram showing an exploded view of components of a movable carriage 116 configured to engage the elongate beam element 102. According to the present example, the movable carriage 116 includes a main body 301 and a drive system 302 that includes a drive shaft 308 and a rotatable element 306. The movable carriage 116 also includes a lock element 304.

As described above, the movable carriage 116 is designed to move along the elongate beam element 102. To accomplish this, the rotatable element 306 of the drive system 302 is inserted into a recess 316 on the side of the main body 301 of the movable carriage 116 that coincides with the engagement feature 106 on the elongate beam element 102. In the present example, the rotatable element 306 is a male helical screw having engagement features 314 while the engagement elements 107 on the beam element 102 take the partial form of a female helical thread of the same type. The rotatable element 306 is held in place with a drive shaft 308 that pins the rotatable element 306 within the movable carriage 116. The drive shaft 308 extends through holes 318 (only one is shown) on opposing sides of the recess 316 and through a center opening 320 of the rotatable element 306. Once assembled, the movable carriage 116 is unable to slide along the elongate beam element 102 because of mechanical interference between the engagement features 314 and the engagement elements 107. In some embodiments, the lock element 304 may prevent the rotation of the rotatable element 306. Rotation of the rotatable element 306 will cause the movable carriage 116 to be driven along the beam element 102. In some examples, when the rotatable element 306 is not snapped into place within the recess 316 of the movable carriage 116, the movable carriage 116 can slide freely along the beam element 102.

According to the present example, the lock element 304 is inserted into the same recess 316 as the rotatable element 306 to prevent the unintended rotation of the rotatable element 306. In some examples, the lock element 304 is configured to lock the rotatable element 306 from being rotated in either direction. In one example, the lock element 304 is configured to allow for rotation in one direction but not both directions in manner such as a ratchet. In some examples, the lock element 304 provides for a manual override such that when an external force is applied to the lock element 304, the lock element 304 unlocks the rotatable element 306. The lock element will be discussed in greater detail below.

Figure 4:
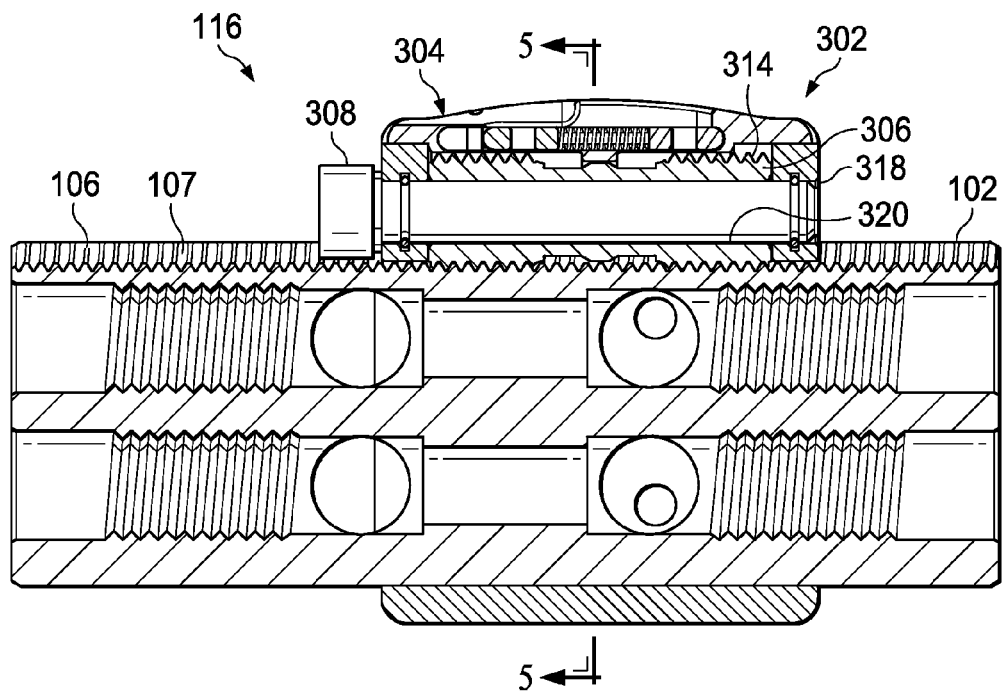
FIG. 4 is a diagram showing a cross-sectional view of the movable carriage on a beam element according to one example of principles described herein.

FIG. 4 is a diagram showing a cross-sectional view of the movable carriage 116. FIG. 4 illustrates the rotatable element 306 engaged with the engagement feature 106 of the beam element 102. In some embodiments, the rotatable element 306 engages with the drive shaft 308 such that rotation of the drive shaft 308 causes corresponding rotation of the rotatable element 306. For example, in some embodiments, the drive shaft 308 has a non-circular cross-section that engages a non-circular central opening 320 in cross-section of the rotatable element 306. Accordingly, the drive shaft 308 and the rotatable element 306 rotate together. In some examples, the cross-sections are D-shaped. In other examples, they have other interfering or non-circular shapes. In some cases, loading that is applied to the movable carriage 116 is transferred into the drive system 302 engaged with the beam element 102.

Figure 5:
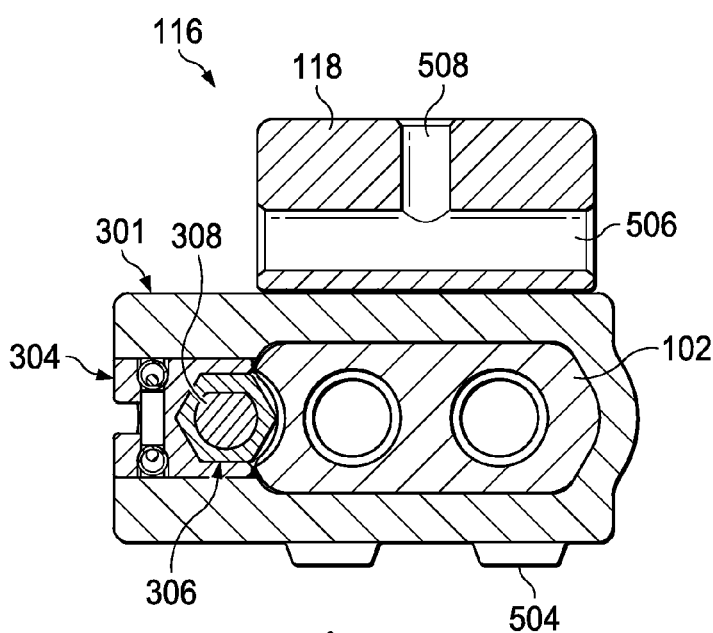
FIG. 5 is a diagram showing a different cross-sectional view along lines 5-5 in FIG. 4 of the movable carriage according to one example constructed according to principles described herein.

FIG. 5 is a diagram showing a different cross-sectional view of the movable carriage 116, particularly, through line 5-5 of the device shown in FIG. 4. FIG. 5 shows a polygonal portion 502 of the rotatable element 306. The polygonal portion 502 is designed to fit with a lock element 304 as will be described in further detail below. The view also illustrates the non-circular drive shaft 308 positioned within the center opening 320 of the rotatable element 306. FIG. 5 also shows the holes 504 that can be used to secure the anchor block 118 to the main body 301 of the movable carriage 116. Such holes 504 can be positioned on both sides of the body. In the present view, the holes are not seen on the top because the anchor block 118 is shown secured to the main body 301. The holes 504 may be formed in bosses that project from the surface of the body. The anchor block 118 may include receiving bores that receive the bosses enabling easy and simple alignment of the anchor block 118 and the carriage. In some embodiments, such as the one shown, the bosses are frusto-conically shaped to enable simple matchup of components.

As illustrated in the cross-sectional view, the anchor block 118 includes a passage 506 through which bone anchors (e.g. 114, FIG. 1) may be placed. The bone anchors 114 can then be locked in place through use of a set screw (not shown) that is placed into passage 508.

Figure 6:
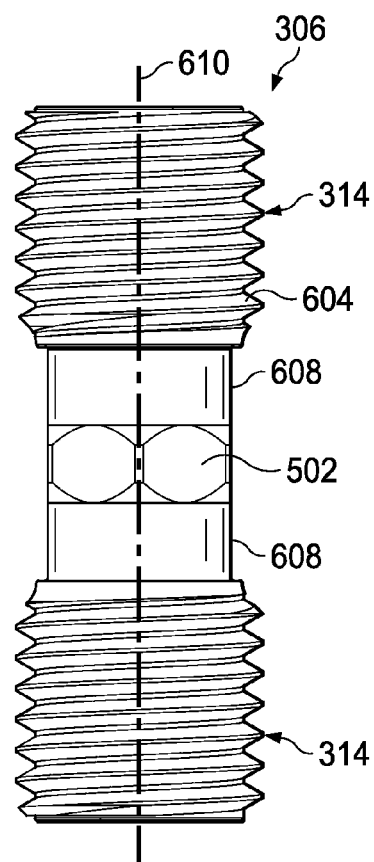
FIG. 6 is a diagram showing an illustrative rotatable element of a drive system according to one example constructed according to principles described herein.

FIG. 6 is a diagram showing an illustrative rotatable element 306 of the drive system 302. According to the present example, the rotatable element 306 includes an engagement feature 314 that includes engagement elements 604 designed to engage an engagement feature (e.g. 106, FIG. 1) of a beam element (e.g. 102, FIG. 1). In this example, the engagement elements 604 are male helical threads.

The rotatable element 306 also includes a non-circular locking portion, shown as a polygonal portion 502 such as a hex portion. The polygonal portion 502 has flat edges that when engaged with tabs of a lock element (e.g. 304, FIG. 3), prevent rotation of the rotatable element 306. On both sides of the polygonal portion 502 are circular portions 608. When the tabs of the lock element (e.g. 304, FIG. 3) are placed over the circular portions 608, rotation of the rotatable element 306 is allowed.

Figure 7C:
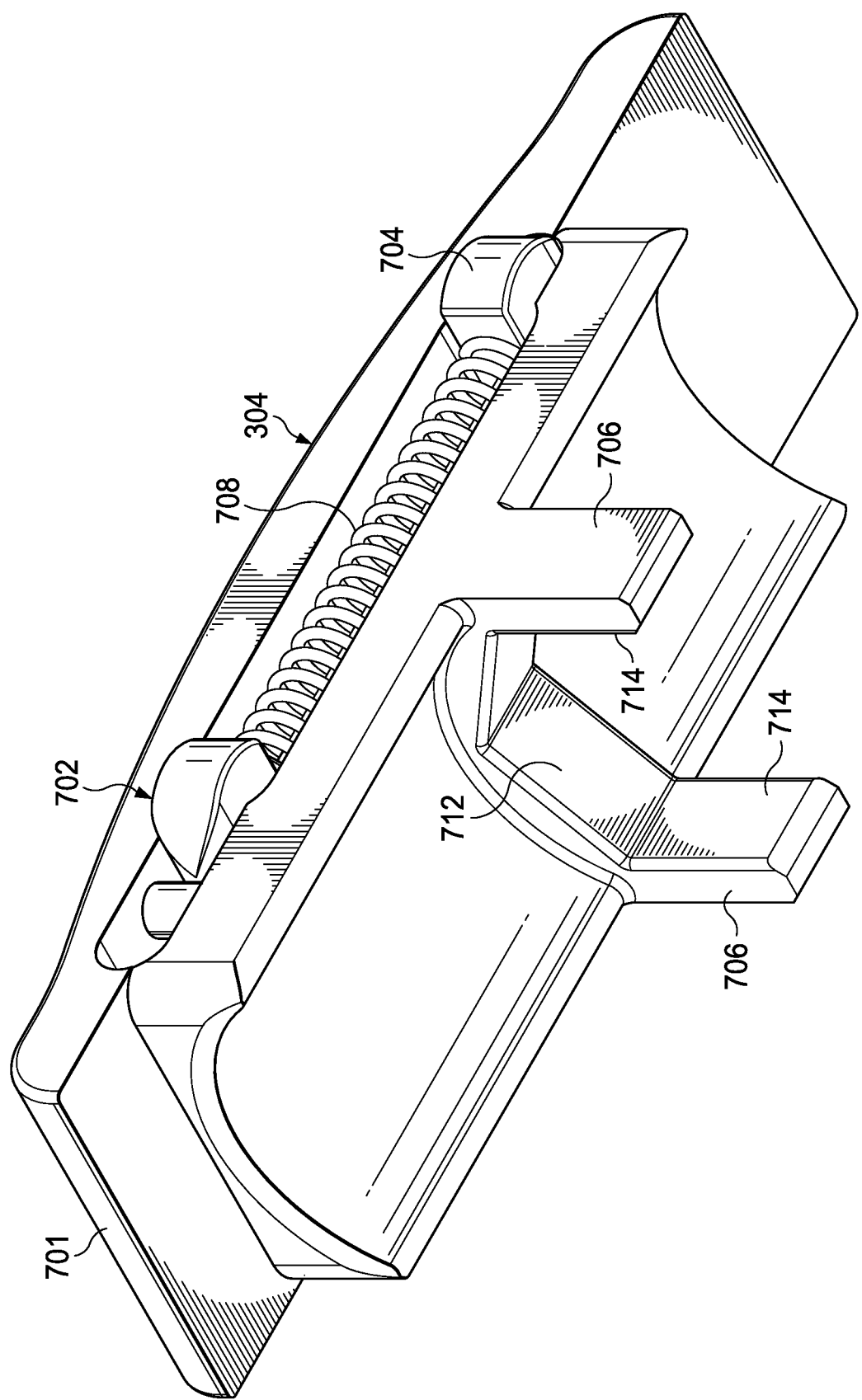

FIGS. 7A, 7B, and 7C are diagrams showing an illustrative lock element 304. FIG. 7A is a top view of the lock element 304, FIG. 7B is a cross-sectional view of the lock element 304 along line 7B-7B, and FIG. 7C is a perspective view of the lock element 304. According to the example shown, the lock element 304 includes a body 701 that houses two spring-loaded key elements 702 that are biased away from each other with a bias element 708. The key elements 702 include tabs 704 that extend outwardly on opposing sides of the body 701. When the lock element 304 is inserted into the recess 316 of the movable carriage (e.g. 116, FIG. 1), the key elements 702 are pressed toward each other such that the tabs 704 of the key elements 702 can fit into the recess 316. The key elements 702 are aligned to fit within the slots 322 in the recess shown in FIG. 3. After passing into the recess 316, the key elements 702 are released and the bias element 708 forces the key elements 702 away from each other such that the tabs 704 extend into undercut slots (e.g., 322, FIG. 3) to prevent the lock element 304 from being removed from the movable carriage 116. The lock element 304 includes tabs 706 that are shaped and formed to extend into the recess 316 in a direction transverse to the axis 210 of the elongate beam element 102. These tabs 706 are arranged to prevent rotation of the lock element 304 when desired. With the lock element 304 placed into the recess 316, the tabs 706 extending from the body 701 fit over the polygonal portion 502 of the rotatable element 306 so as to prevent rotation thereof.

FIG. 7B shows the tabs 706 and the bias element 708 that biases the key elements 702 away from each other. In the embodiments shown, the tabs 706 have parallel inner surfaces 714 that engage the polygonal portion 502. In addition, the tabs 706 are connected by a portion of the body 701 having engagement surfaces 712 that may also engage the polygonal portion 502 of the rotatable element 306. This can be seen in the cross-section of FIG. 5. Other arrangements for preventing relative rotation between the rotatable element 306 and the lock element 304 are also contemplated.

To disengage the lock element 304, the body 701 is slid in a direction along the longitudinal axis 610 of the rotatable element 306. A recessed portion 710 within the body 701 allows for easier gripping of the body to move the lock element 304 accordingly. Moving the lock element 304 as such moves the tabs 706 out of engagement with the polygonal portion 502 and into engagement with the circular portion 608, thereby allowing rotation of the rotatable element 306. In addition to the above described example of the lock element 304, other locking mechanisms for securing the rotatable mechanism are contemplated. For example, as will be described in further detail below, the rotatable element 306 and the lock element 304 may form a ratchet mechanism.

Figure 8A:
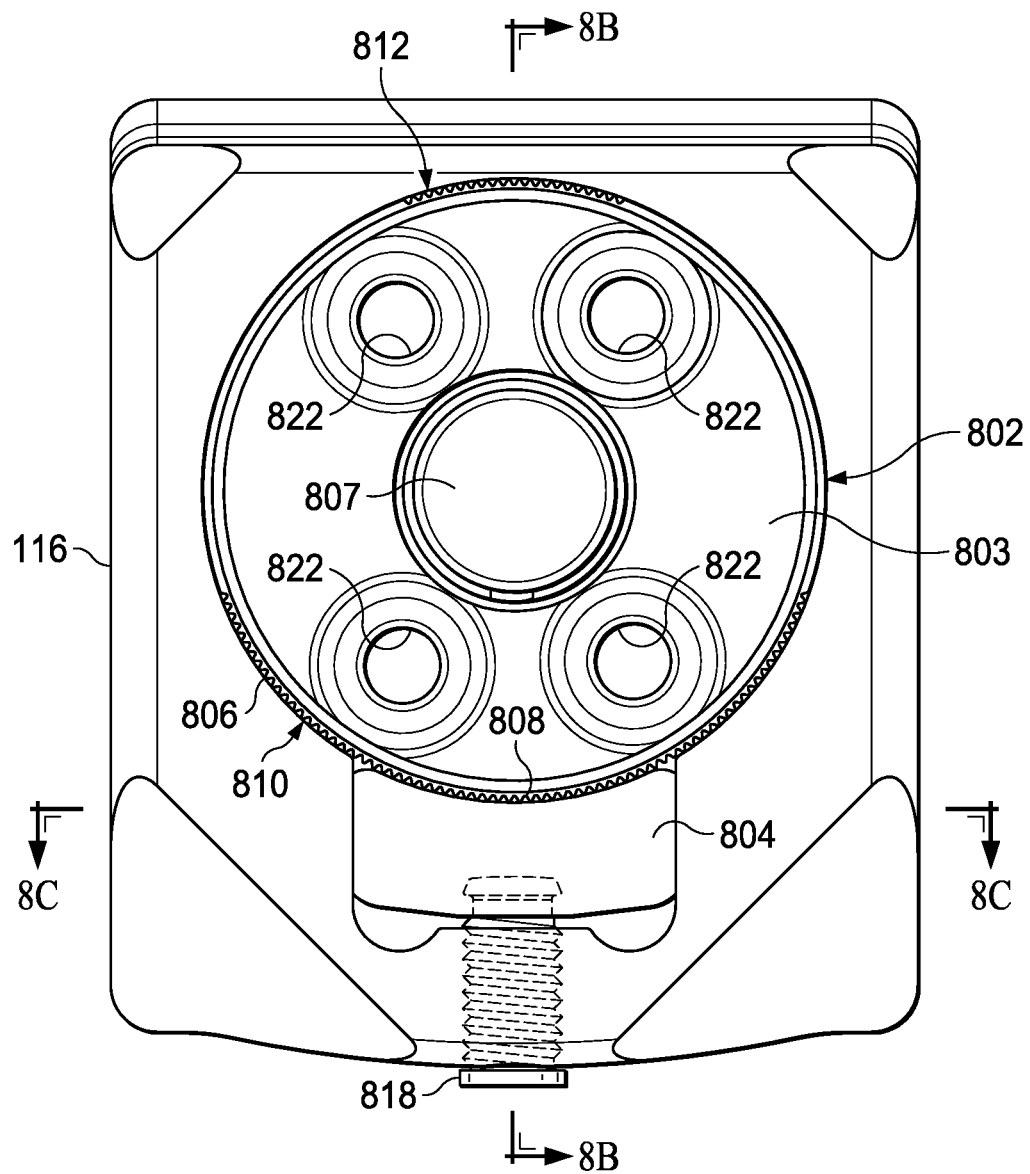
FIGS. 8A, 8B, and 8C are diagrams showing various views of a movable carriage with a rotating mechanism according to one example constructed according to principles described herein.
Figure 8B:
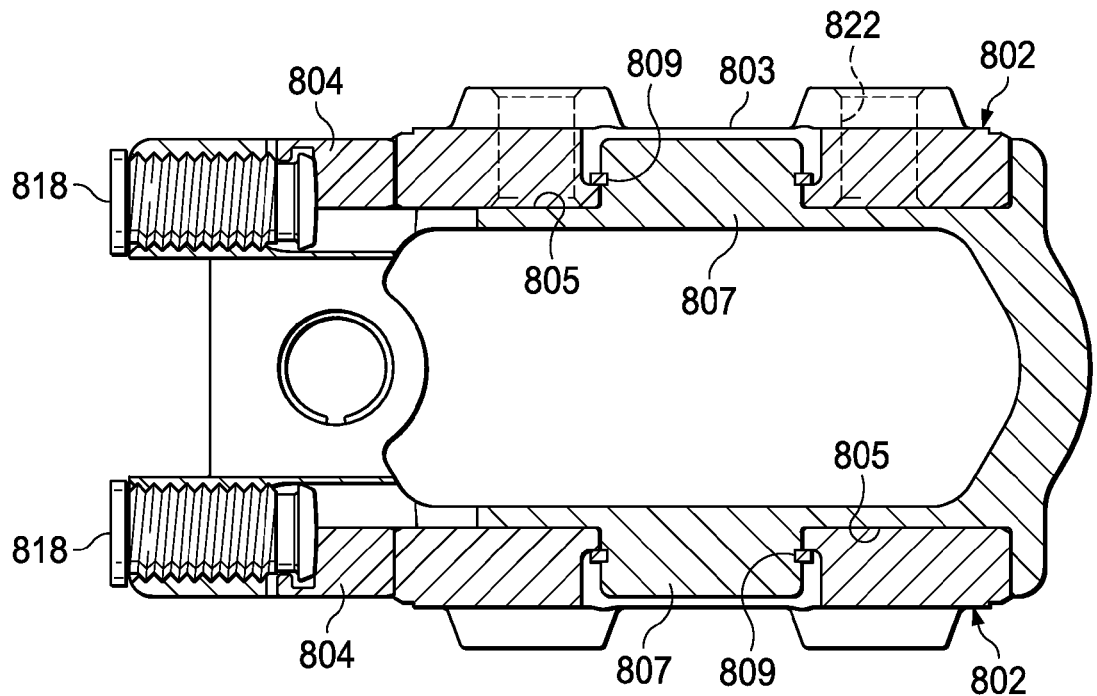
Figure 8C:
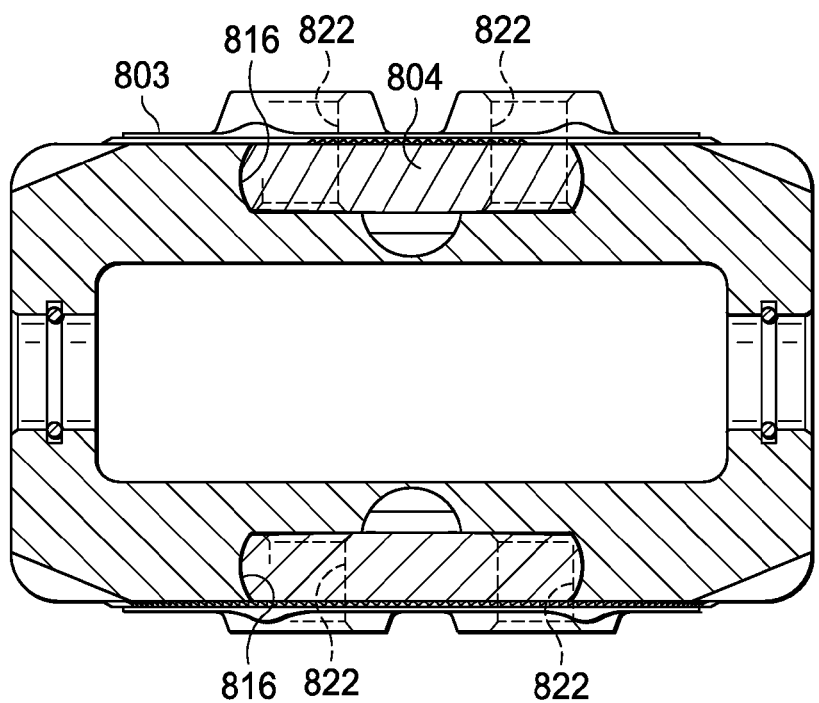

FIGS. 8A, 8B, and 8C are diagrams showing various views of a movable carriage 116 with a rotating mechanism 802. Here, for clarity, the movable carriage 116 is shown without the lock element 304. FIG. 8A illustrates a top view of the rotating mechanism 802, FIG. 8B illustrates a cross-section along line 8B-8B and FIG. 8C illustrates a cross-section along line 8C-8C. The rotating mechanism 802 is arranged to connect to the anchor block 118 (FIG. 1) and permit the anchor block 118 to rotate relative to the movable carriage 116 and in relation to the elongate beam element 102. In so doing, the bone anchors 114 carried by the anchor block 118 may be rotated and angled to a desired position to facilitate treatment of the patient. In the example shown, the movable carriage 116 includes two rotating mechanisms 802, one on each of two opposing sides. Typically, the anchor block 118 is attached to only one side. However, some treatment regimes may include anchor blocks on both sides.

According to the present example, the rotating mechanism 802 includes a cylindrical turntable 803 fit within a corresponding recess 805 that is machined into a side of the movable carriage 116. Here, the recess is formed so that a boss 807 projects in a central region of the recess with the turntable 803 rotatable about the boss 807. The cylindrical turntable 803 may be secured to the movable carriage 116 with a snap ring 809.

The turntable 803 includes a first set 810 of gear teeth 806 that are designed to match and engage with a corresponding set of engagement features 808 on a radially driven key 804. When the engagement features 808 of the key 804 are engaged with the gear teeth 806, they prevent rotation of the turntable 803. The key 804 fits within a pocket 816 in the movable carriage 116. The pocket 816 intersects with the cylindrical recess 805 that holds the turntable 803. The key 804 is driven into and out of engagement with the turntable 803 through the action of a captured set screw 818.

In the present example, there are two sets 810, 812 of gear teeth 806. The first set 810 of gear teeth 806 spans a larger arc and allows for rotation to be set across a range of angles. The second set 812 of gear teeth 806 is smaller and allows for ease of setting the turntable 803 into a given rotation position as indicated above. The turntable 803 can be positioned on one side of the movable carriage or both sides of the movable carriage 116. In some examples, however, the turntable 803 may not be present on the movable carriage 116. The turntable 803 includes a set of holes 822 that allow for connection to an anchor block (e.g. 118, FIG. 1). In some aspects, the holes 822 are threaded and receive bolts extending from or through the anchor block 118. As can be seen in FIG. 8A, the holes 822 are spaced farther in a longitudinal direction than in the lateral direction. Here, the holes 822 are formed as bosses that project from the surface of the turntable. The anchor block 118 may include receiving bores that receive the bosses enabling easy and simple alignment of the anchor block 118 and the carriage. With the anchor block 118 secured to the turntable 803, the bone anchors 114 extending from the anchor block can be angulated with respect to the beam element 102.

Figure 9A:
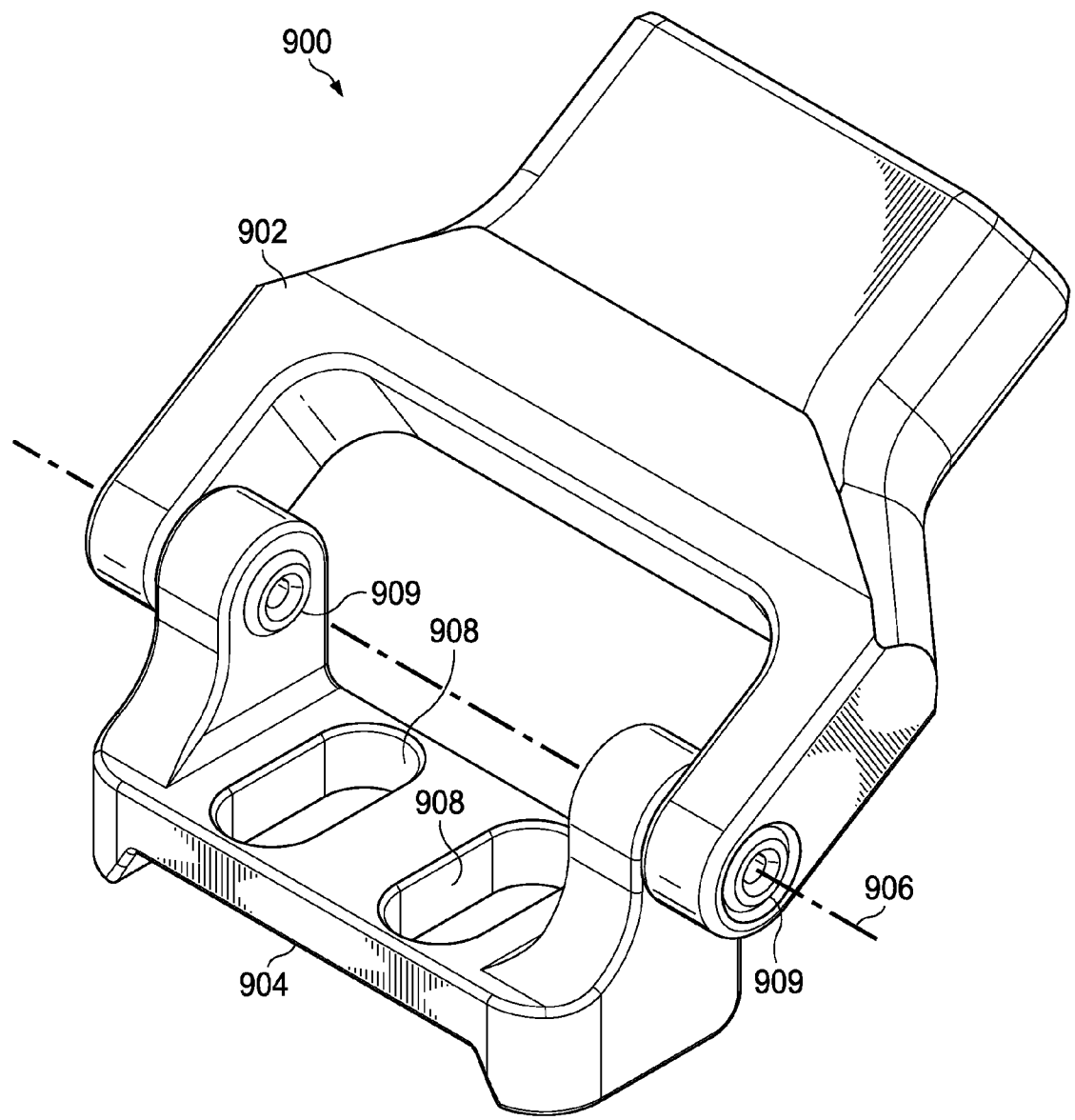
FIGS. 9A and 9B are diagrams showing an illustrative slotted hinge element and an illustrative rotational hinge element according to examples constructed according to principles described herein.
Figure 9B:
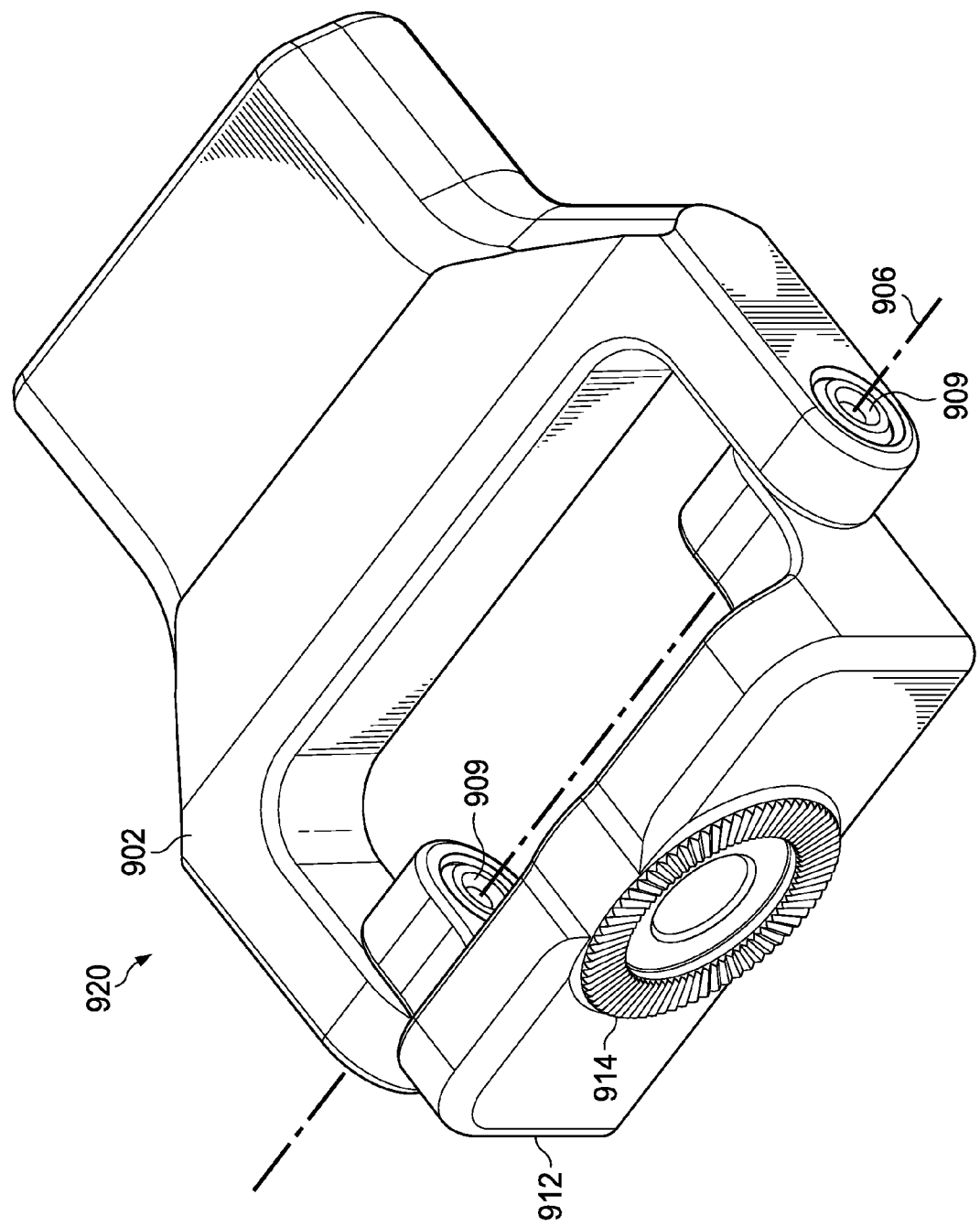

FIGS. 9A and 9B are diagrams showing an illustrative slotted hinge element 900 and an illustrative rotational hinge element 920. FIG. 9A illustrates the slotted hinge element 900. The slotted hinge element 900 includes a hinge bracket 904 and a hinge yoke 902. The hinge bracket 904 includes a pair of slots 908 that allow the hinge element 904 to be connected to the end of a beam element (e.g., 102, 202), a connector element (e.g. 108), or an anchor block (e.g. 110). Thus, the slots 908 can be sized and spaced to allow for such a connection. The hinge bracket 904 rotates about an axis 906 formed by a hinge or pivot connection with respect to the hinge yoke 902. The axis 906 is defined by hinge pins 909. In some embodiments, the hinge pins 909 are hollow and can receive a guide pin therethrough. The hinge yoke 902 may be shaped and arranged to connect to a different beam element (e.g. 102, 202) which may be a curved beam element. In some examples, the hinge yoke 902 includes two connection holes (not shown) that may be sized and shaped to align with the through-holes 218 of the elongate beam element 102. The slots 908 allow for placement of the slotted hinge element 900 anywhere along their length or within their envelope. The slots 908 may be straight in form (as illustrated) to allow for simple translation, or curved to allow for rotation about an arbitrary point in space or a combination of straights and curves to allow for a continuum of rotational centers. Because the slotted hinge element 900 can be connected to either a beam element (e.g. 102, 202), the movable carriage (e.g. 106, FIG. 1), the connector element (e.g. 108, FIG. 1), or an anchor block (e.g. 110, 118), a chain of such slotted hinge elements 900 having multiple degrees of freedom can be achieved.

FIG. 9B illustrates the rotational hinge element 920. The rotational hinge element 920 includes a hinge bracket 912 with a rotating connector element 914. The rotating connector element 914 is configured to connect to a beam element (e.g., 102, 202), a connector element (e.g. 108), or an anchor block (e.g. 110) while allowing the hinge bracket 912 to rotate with respect to the component to which it is attached. The hinge bracket 912 is also connected to a hinge yoke 902. In this embodiment, the rotating connector element 914 is formed of a series of radially extending splines configured to interdigitate with corresponding splines on the opposing component. The rotating connector element 914 may have a knurled surface, a roughened surface, or other friction inducing features that allow the hinge yoke 902 to securely connect in a desired orientation.

Figure 10A:
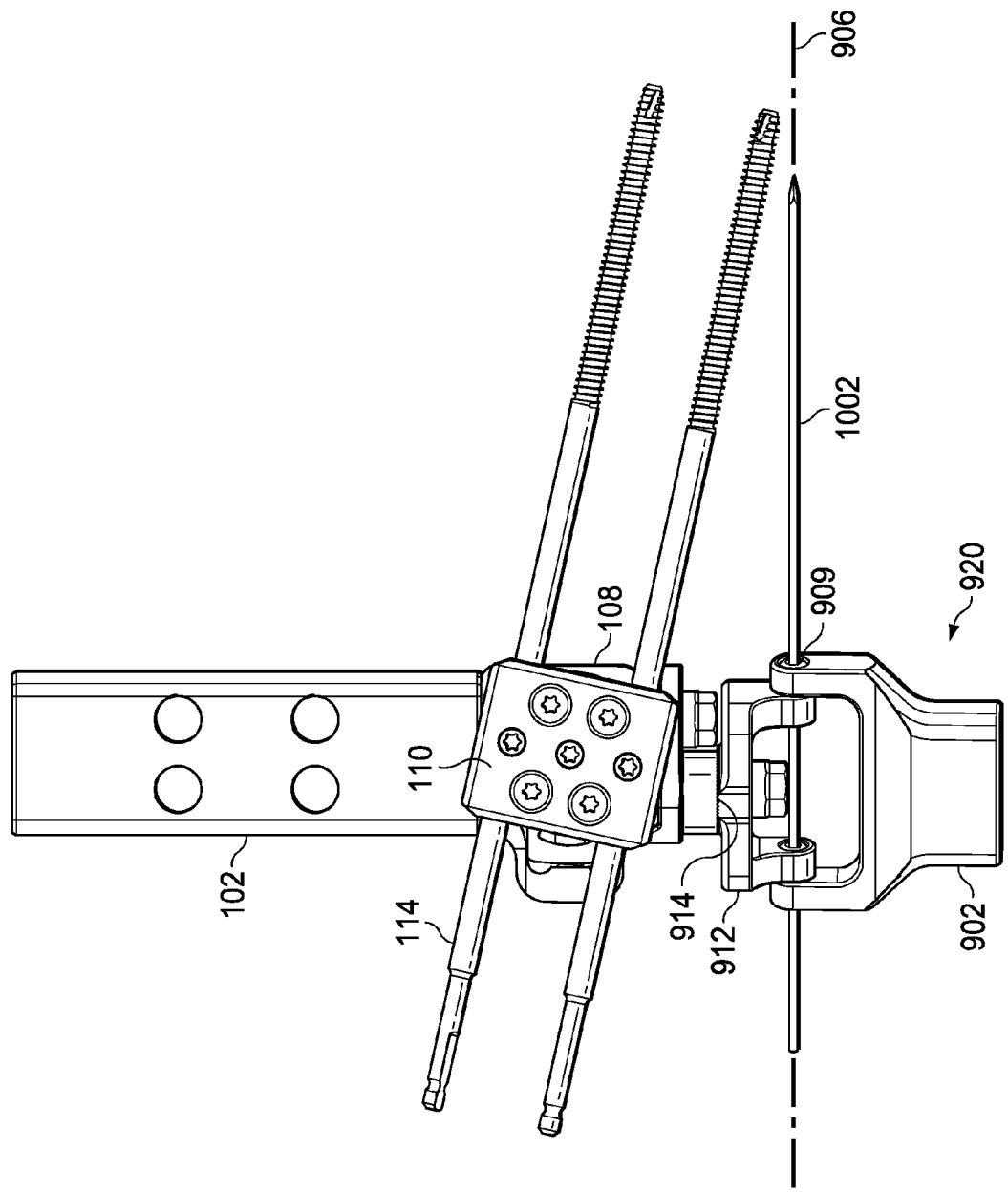
FIGS. 10A and 10B are diagrams showing an illustrative rotational hinge element connected to a fixed connector element at an end of a beam element according to one example constructed according to principles described herein.
Figure 10B:
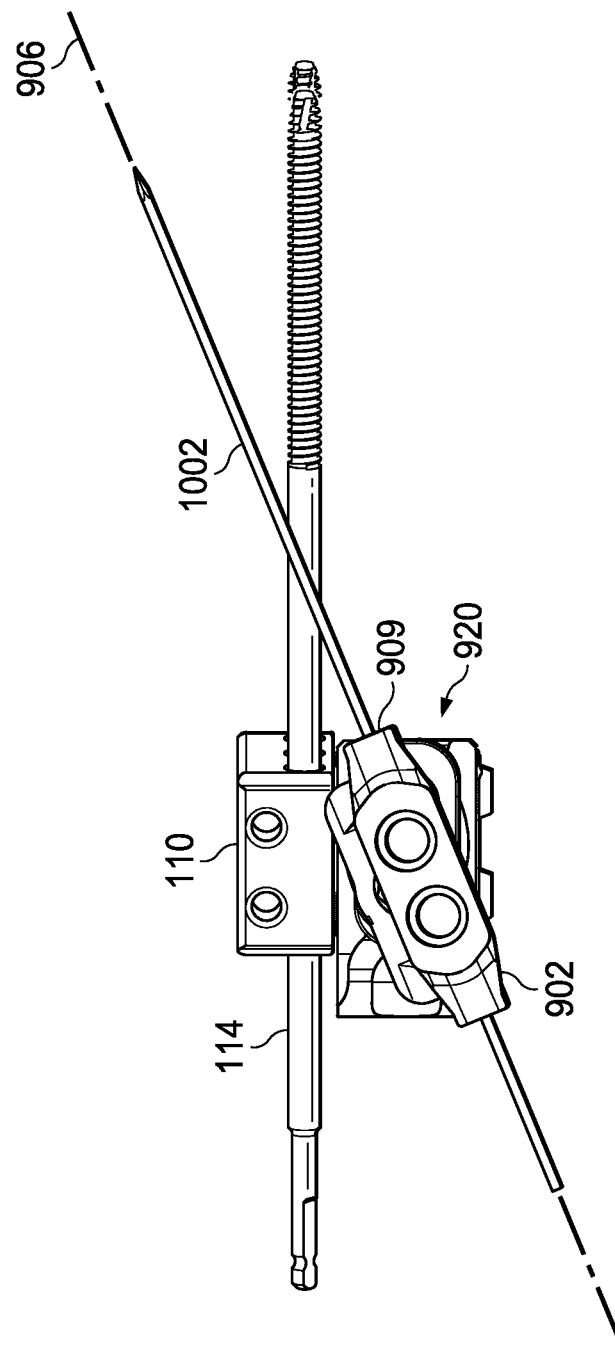

FIGS. 10A and 10B are diagrams showing an illustrative rotational hinge element 920 connected to a connector element 108 at an end of a beam element 102. FIG. 10A illustrates a top view and FIG. 10B illustrates a side view. In this example, the rotational hinge element 920 is connected to the connector element 108. Additionally, a temporary guide pin 1002 is placed along the axis 906 through the hinges. In one example, the temporary guide pin 1002 can temporarily be inserted at the axis of rotation of a patient's knee. This allows the axis 906 of the rotational hinge element 920 to be aligned with the axis of rotation of the knee. For example, in the case where the fixation system 100 is to be used to perform operations on the femur, the hinge yoke 902 can be connected to a device that is attached to the part of the leg distal to the knee, with the axis 906 appropriately aligned with the axis of the knee.

Figure 11A:
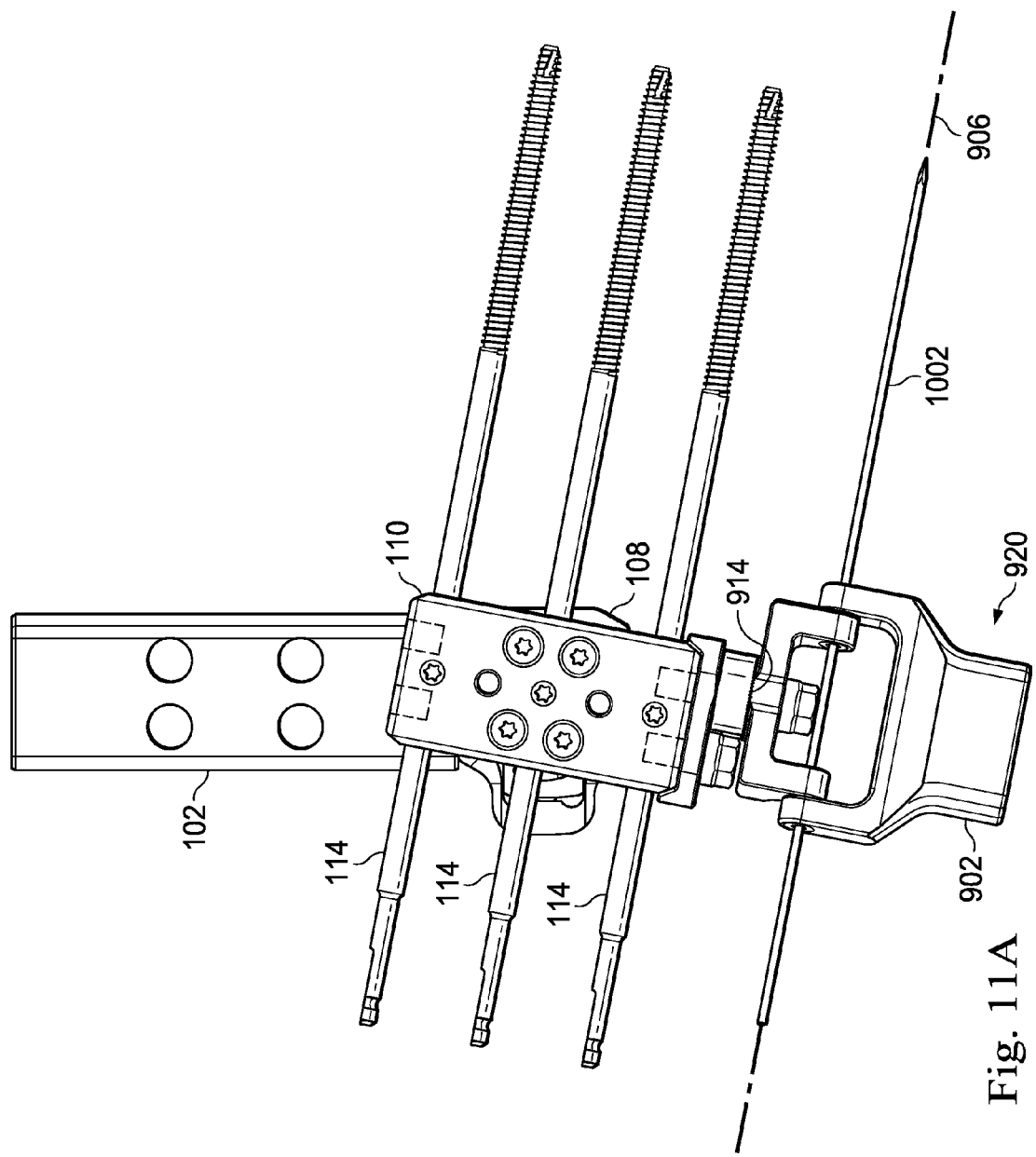
FIGS. 11A and 11B are diagrams showing an illustrative rotational hinge element connected to an anchor block that is connected to a fixed connector element at an end of a beam element according to one example constructed according to principles described herein.
Figure 11B:
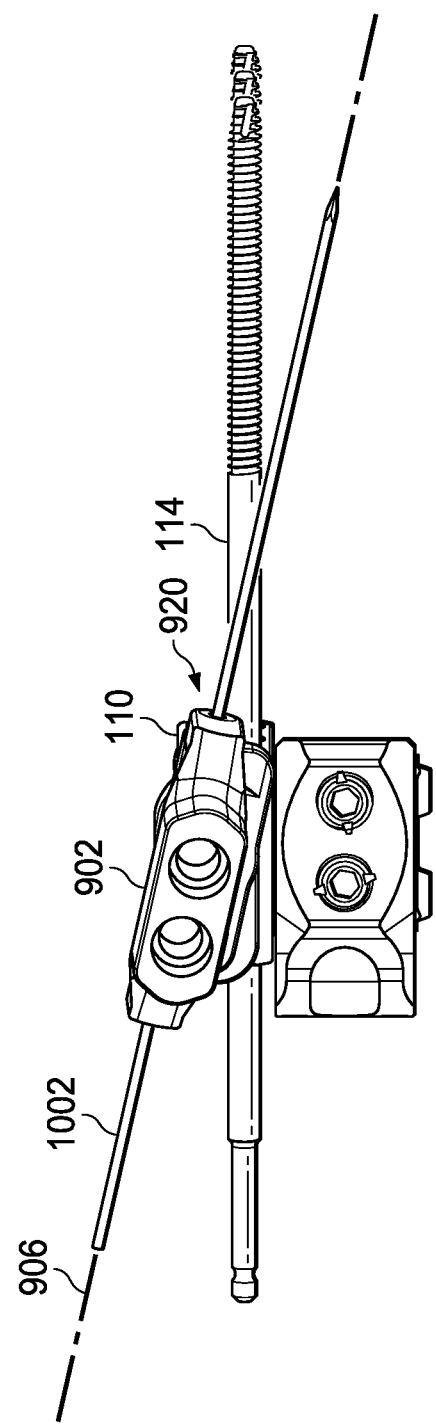

FIGS. 11A and 11B are diagrams showing an illustrative rotational hinge element 920 connected to an anchor block 110 that is connected to a connector element 108 at an end of the elongate beam element 102. FIG. 11A illustrates a top view and FIG. 11B illustrates a side view. In this example, the anchor block 110 is connected to the connector element 108 through a rotating mechanism 802 such as a turntable (e.g. 803, FIG. 8). Thus, the rotational hinge element 920 moves with the anchor block 110 as the anchor block 110 rotates with respect to the connector element 108.

Figure 12A:
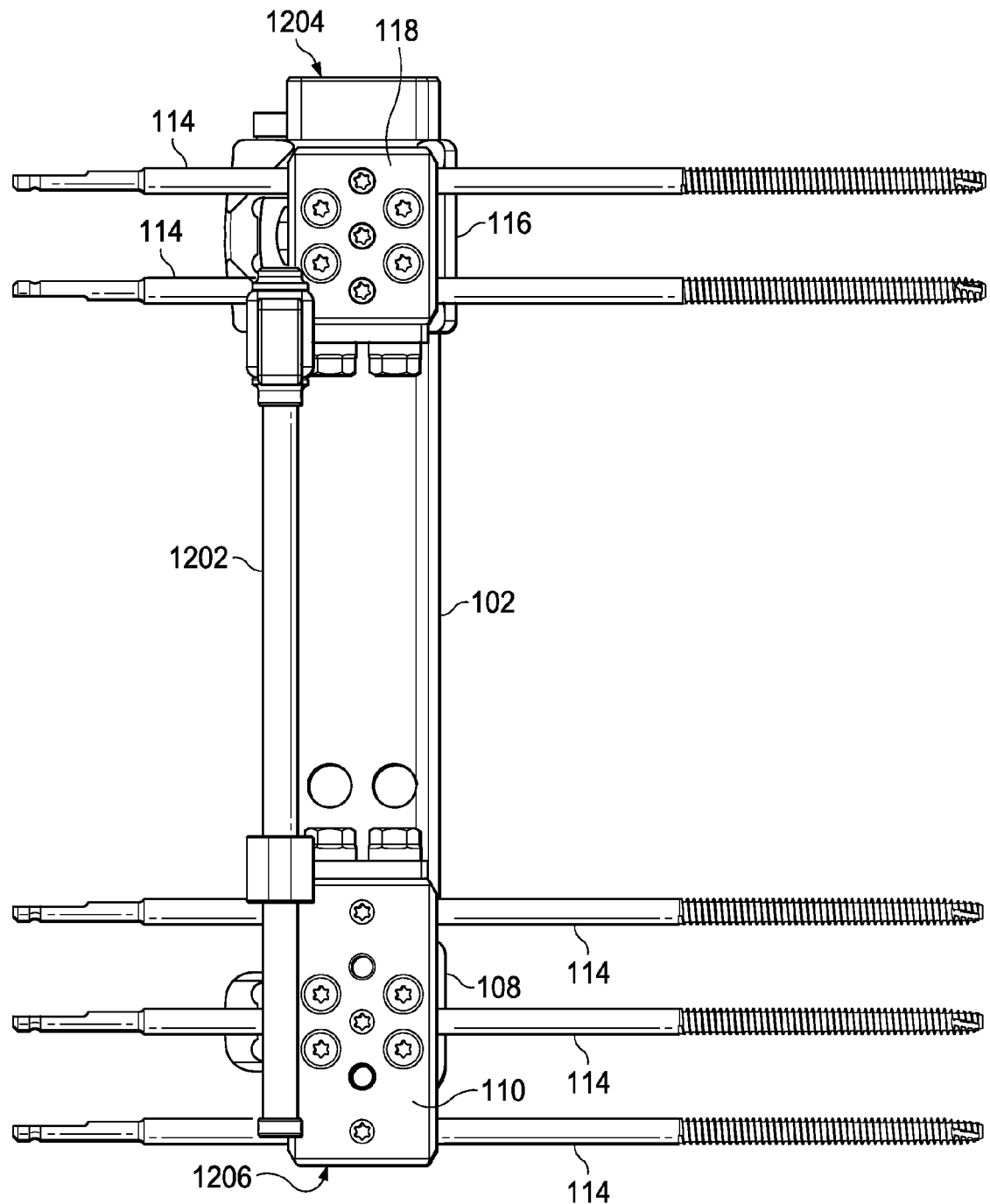
FIGS. 12A and 12B are diagrams showing a strut configured to cause rotation of an anchor block according to one example constructed according to principles described herein.
Figure 12B:
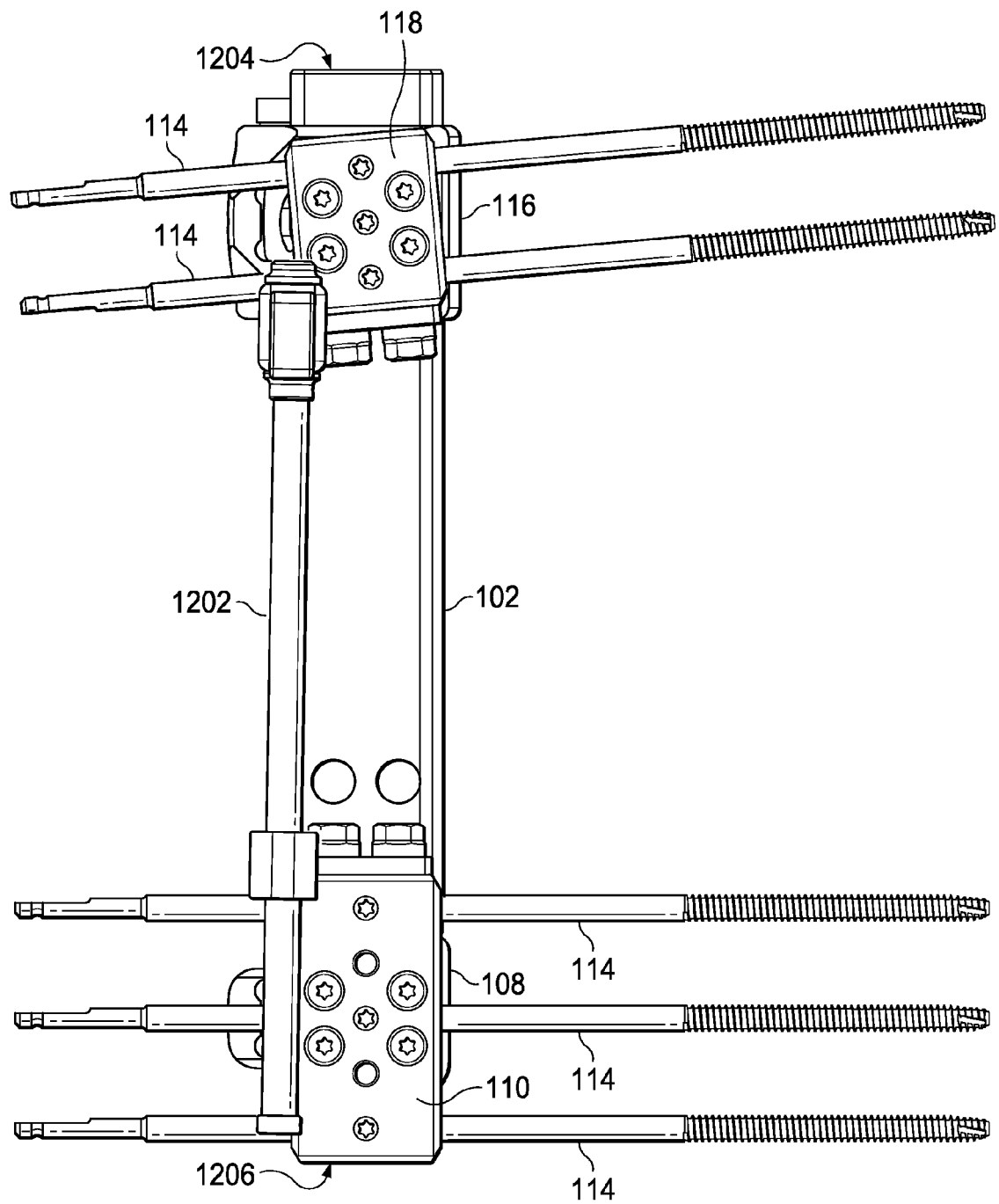

FIGS. 12A and 12B are diagrams showing a strut assembly 1202 configured to cause rotation of anchor block 118. Thus, the strut assembly 1202 is used as a means of angulation for the set of bone anchors 114. In the present example, the beam element 102 is shown with a fixed connector element 108 attached to one end 1206. The connector element 108 may have either a fixed anchor block interface or a turntable (e.g. 803, FIG. 8A) in the locked state. At the other end 1204 of the beam element 102, a movable carriage 116 is positioned along and fixed to the beam element 102 at a particular location. The movable carriage 116 has a rotating turntable 803 to connect to the anchor block 118. The strut assembly 1202 is attached to one common interface of each of the two anchor blocks 110, 118. The line of action of the strut assembly 1202 is offset from the axis of rotation of the turntable 803. In this configuration the strut-to-block connection includes a revolute joint, the axis of which is parallel to the axes of the turntable 803, resulting in a triangular linkage arrangement. One link is the beam element 102, the second is the length of the strut assembly 1202 and the third is the offset distance between the axis of rotation of the turntable 803 and the axis of the attached strut revolute joint. The change in the length of any side of a triangle while the other two sides remain fixed in length will result in the change in all of the angles of the triangle. The result is that the anchor block 118 is forced to rotate relative to the beam element 102. Other means of achieving the same are also contemplated.

Figure 13:
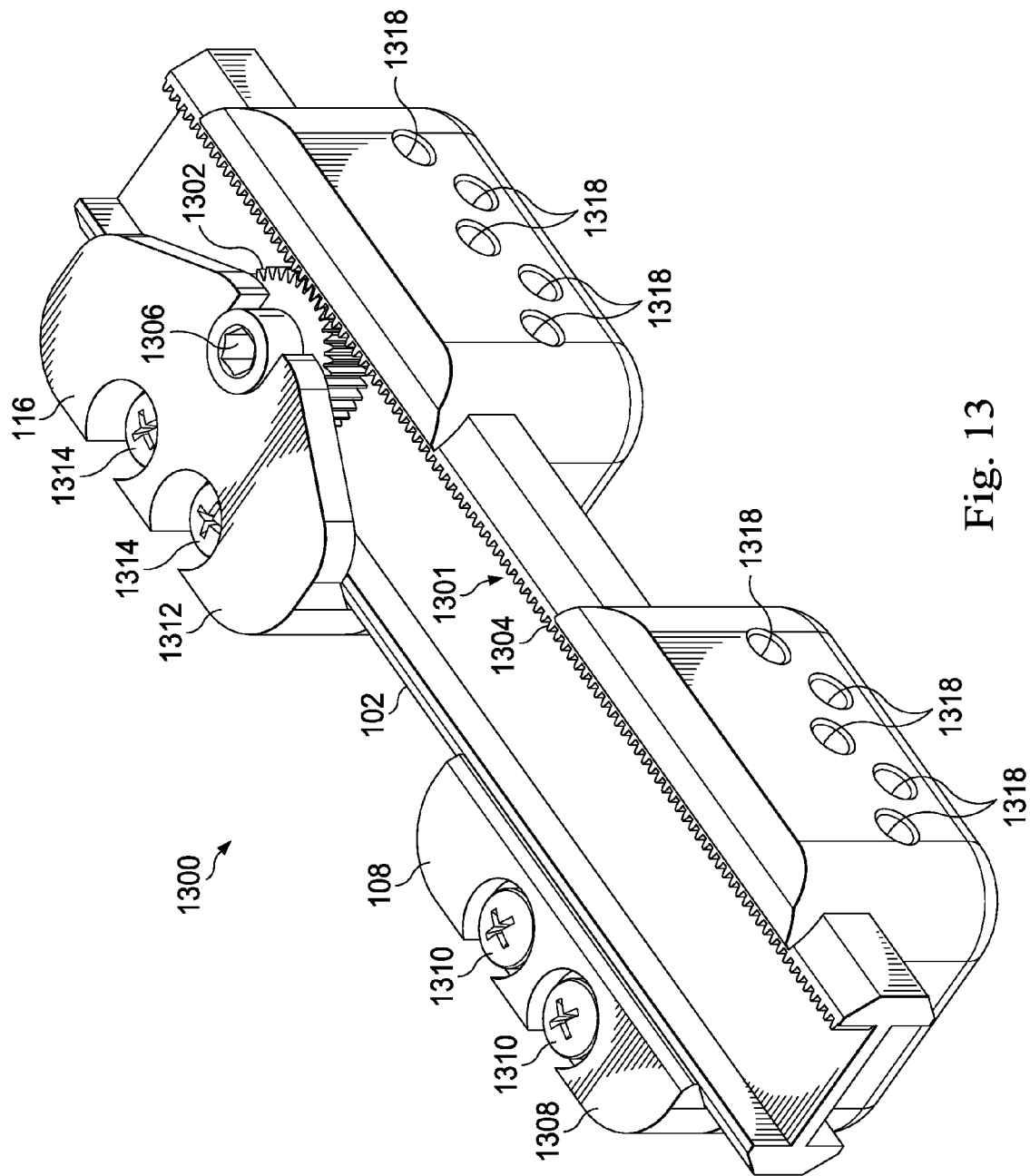
FIG. 13 is a diagram showing an illustrative beam element with a set of straight teeth as an engagement feature according to one example constructed according to principles described herein.

FIG. 13 is a diagram showing a fixation system 1300 with an illustrative elongate beam element 102 in a different configuration with a set of straight teeth 1304 as an engagement feature 1301. The fixation system 1300 includes a fixed connector element 108 and a movable carriage 116 that is driven along the beam element 102 through use of a rotatable gear 1302 that engages with the straight teeth 1304. Accordingly, the rotation system operations as a rack and pinion system. In the present example, the fixed connector element 108 is fixed to the beam element 102 with a locking plate 1308 that is configured to clamp to the beam element 102 when the screws 1310 are tightened. The movable carriage 116 holds the rotatable gear 1302 in a driver plate 1312, which in this embodiment is connected to or forms part of the movable carriage 116 with screws 1314 and partially wraps around the beam element 102. In this example, a hex key can turn the rotatable gear 1302 by inserting the hex key into the key-hole 1306 positioned at the center of the axis of rotation of the rotatable gear 1302. In some examples, the driver plate 1312 incorporates a ratchet mechanism or a locking element that would prevent the rotatable gear 1302 from turning in either one or both directions to control when and how the movable carriage 116 is moved along the beam element 102. While the present example illustrates a single rotatable gear 1302, other examples may have multiple gears. Anchor holes 1318 are arranged to receive bone anchors (e.g. 114, FIG. 1). It is noted that a rack and pinion system or straight teeth can be used on all embodiments disclosed herein.

Figure 14:
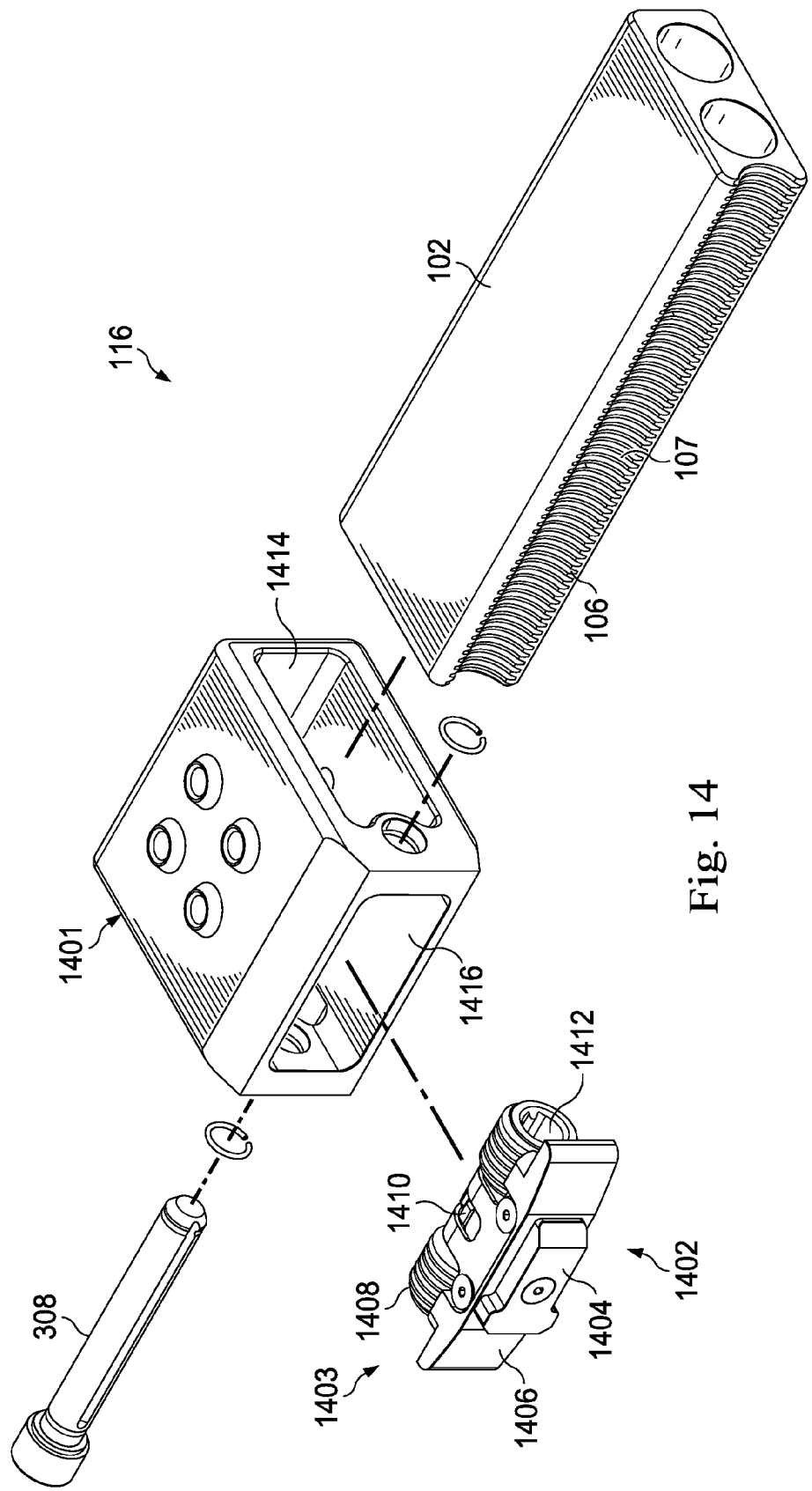
FIG. 14 is a diagram showing an exploded view of a movable carriage with a ratchet mechanism and a beam element according to one example constructed according to principles described herein.
Figure 15:
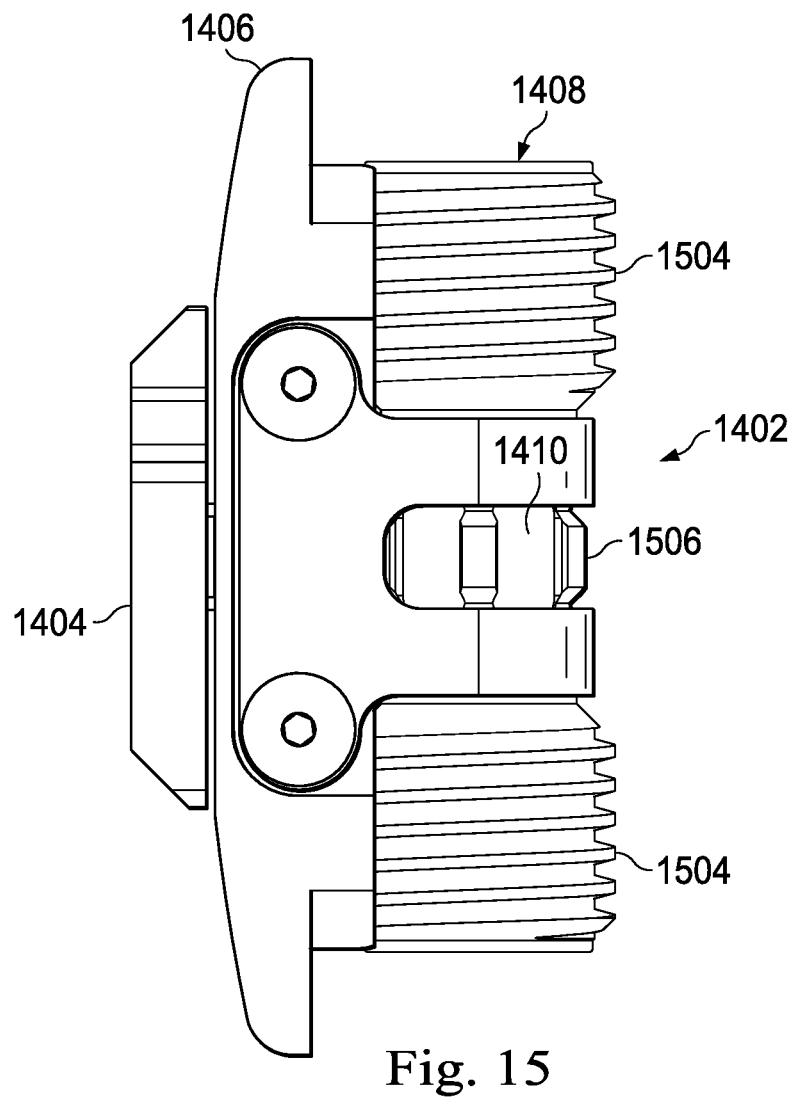
FIG. 15 is a diagram showing a side view of the ratchet mechanism according to one example constructed according to principles described herein.
Figure 16:
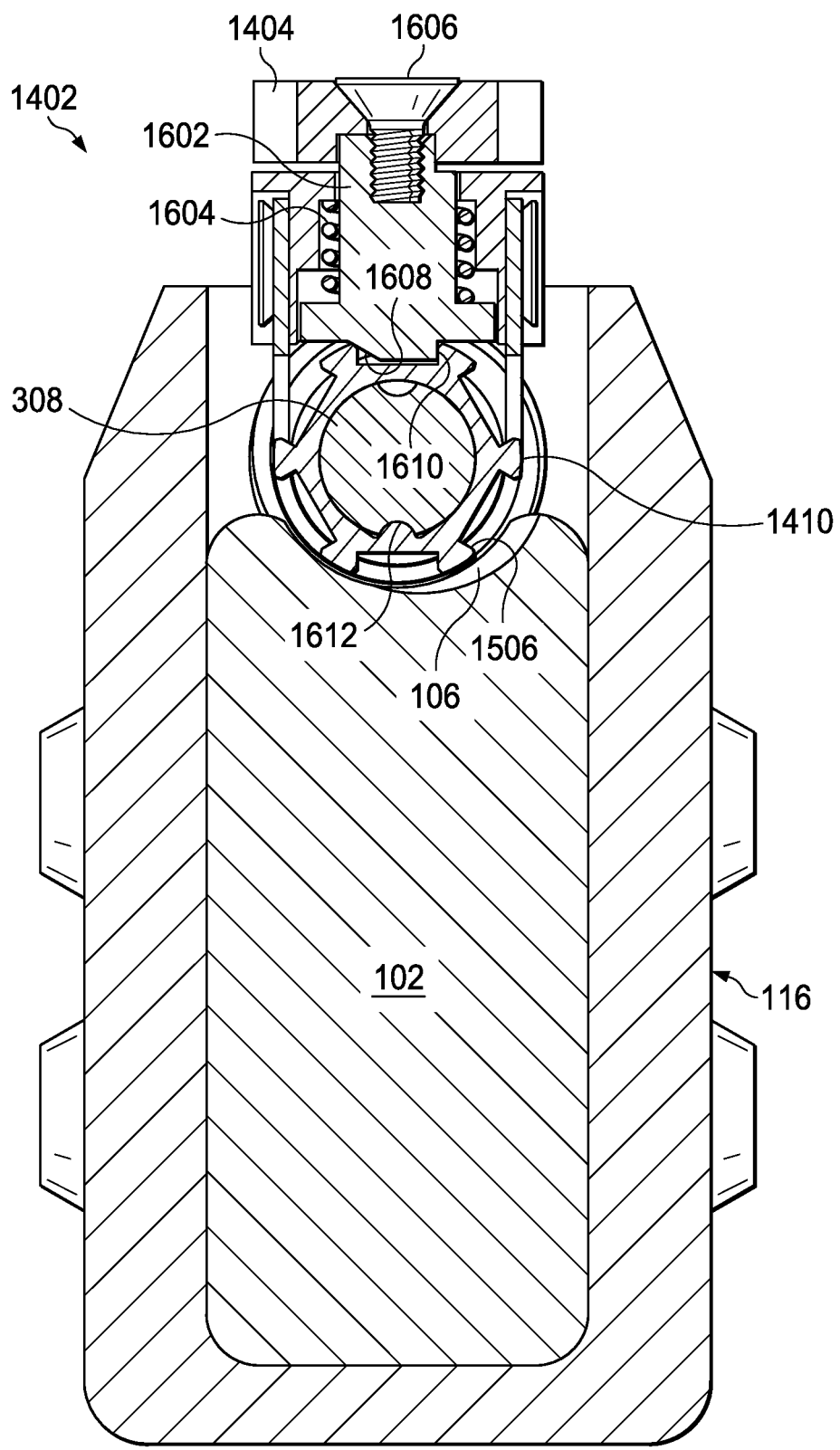
FIG. 16 is a diagram showing a cross-sectional view of the movable carriage with the ratchet mechanism and the beam element according to one example constructed according to principles described herein.

FIGS. 14-16 show an alternative movable carriage 116 with the elongate beam element 102. FIG. 14 is a diagram showing an exploded view of a movable carriage 116 with a main body 1401 and a drive system 1403 with a ratchet mechanism 1402 used to drive the movable carriage 116 along the beam element 102. In the present example, the ratchet mechanism 1402 includes a body 1406, a direction indicator 1404, and a rotatable element 1408 having a gear 1410 thereon. To assemble the ratchet mechanism 1402 to the movable carriage 116, the ratchet mechanism 1402 is inserted into a recess 1416 in the movable carriage 116. The drive shaft 308 is then inserted into a hole 1412 in the rotatable element 1408 of the ratchet mechanism 1402. Snap-rings may be used to secure the drive shaft 308 in place within the hole main body 1401. The elongate beam element 102 fits within a passage 1414 in the main body 1401.

The direction indicator 1404 in this embodiment is shown with a direction indicating shape that conveys information to a user about which direction the movable carriage 116 might move along the elongate beam element 102. In this embodiment, the shape is shown as an arrow shape. Other shapes, however, are also contemplated.

FIG. 15 is a diagram showing a side view of the ratchet mechanism 1402. The rotatable element 1408 includes engaging portions 1504 and a gear 1410. The engaging portions 1504 include helical threads designed to engage with corresponding threads of the engagement feature 106 on the beam element 102. The gear 1410 includes a number of tooth features 1506 that engage a ratchet element attached to the direction indicator 1404 as will be described in further detail below.

FIG. 16 is a diagram showing a cross-sectional view of the ratchet mechanism 1402. Here, the beam element 102 is within the passage 1414 of the movable carriage 116. The direction indicator 1404 is secured to a ratchet element 1602 via a screw 1606. The ratchet element 1602 is biased against the gear 1410 by a biasing element 1604. The biasing element 1604 may be a spring such as a helical wire form spring, a monolithic mechanical spring, or an elastomer. As can be seen, the gear 1410 includes tooth features 1506 spaced apart with sides forming planes that are parallel on adjacent tooth features 1506. By changing the position of the direction indicator 1404, the ratchet element 1602 allows or prevents rotation of the gear 1410 and thus the rotatable element 1408. Specifically, one side of the ratchet element has a stop surface 1610 shaped to resist sliding when a tooth feature 1506 is pressed against it, while the other side of the ratchet element 1602 has a sloped surface 1608 such that the act of turning the drive shaft 308 presses the ratchet element 1602 away from the rotatable element 1408, thus compressing the biasing element 1604. The tooth feature 1506 then slides across the ratchet element 1602 until it crosses the entire feature. The ratchet element 1602 then snaps into the space between the tooth features 1506, thus clicking into a new resting spot.

In the illustrated configuration, the sloped surface 1608 of the ratchet element 1602 allows for clockwise rotation (from the present view) of the gear 1410. But, the stop surface 1610 on the other side of the ratchet element 1602 will prevent rotation in the counter-clockwise direction. If the ratchet element is turned 180 degrees, which can be done by rotating the direction indicator 1404, the sloped surface 1608 will face the opposite way. Thus, counter-clockwise rotation of the gear 1410 is allowed while clockwise rotation of the gear 1410 is prevented. In some examples, the ratchet element 1602 is designed such that a 90 degree rotation from the present configuration will prevent rotation of the gear 1410 in both directions.

The cross-section of the drive shaft 308 is shown with a key 1612 and keyway used to rotate the drive shaft 308 and thus the rotatable element 1408. In this example, the gear 1410 includes six tooth features 1506. In other examples, however, another number of tooth features 1506 may be used. The amount of tooth features 1506 can be selected based on the pitch of the rotatable element helix and the travel distance desired for each click of the ratchet element 1602.

The ratchet mechanism 1402 allows the drive shaft 308 to rotate the rotatable element 1408 in a single direction. The tooth features 1506 can be designed symmetrically so that the direction that the rotatable element 1408 can be set either way based on the orientation of the ratchet element 1602. Without such a switchable ratchet element 1602, the direction that the movable carriage 116 could move could be changed by removing the entire ratchet mechanism 1402, flipping its direction, and reinserting the ratchet element 1602.

In some examples, two movable carriages may be connected to the beam element 102. One of the carriages can be locked permanently to the beam element 102 by inserting a lock element into the otherwise movable carriage. The other carriage element can be slide-able, lockable or drivable, and so the permanently locked carriage can be created by assembling a lock mechanism into the carriage.

Figure 17:
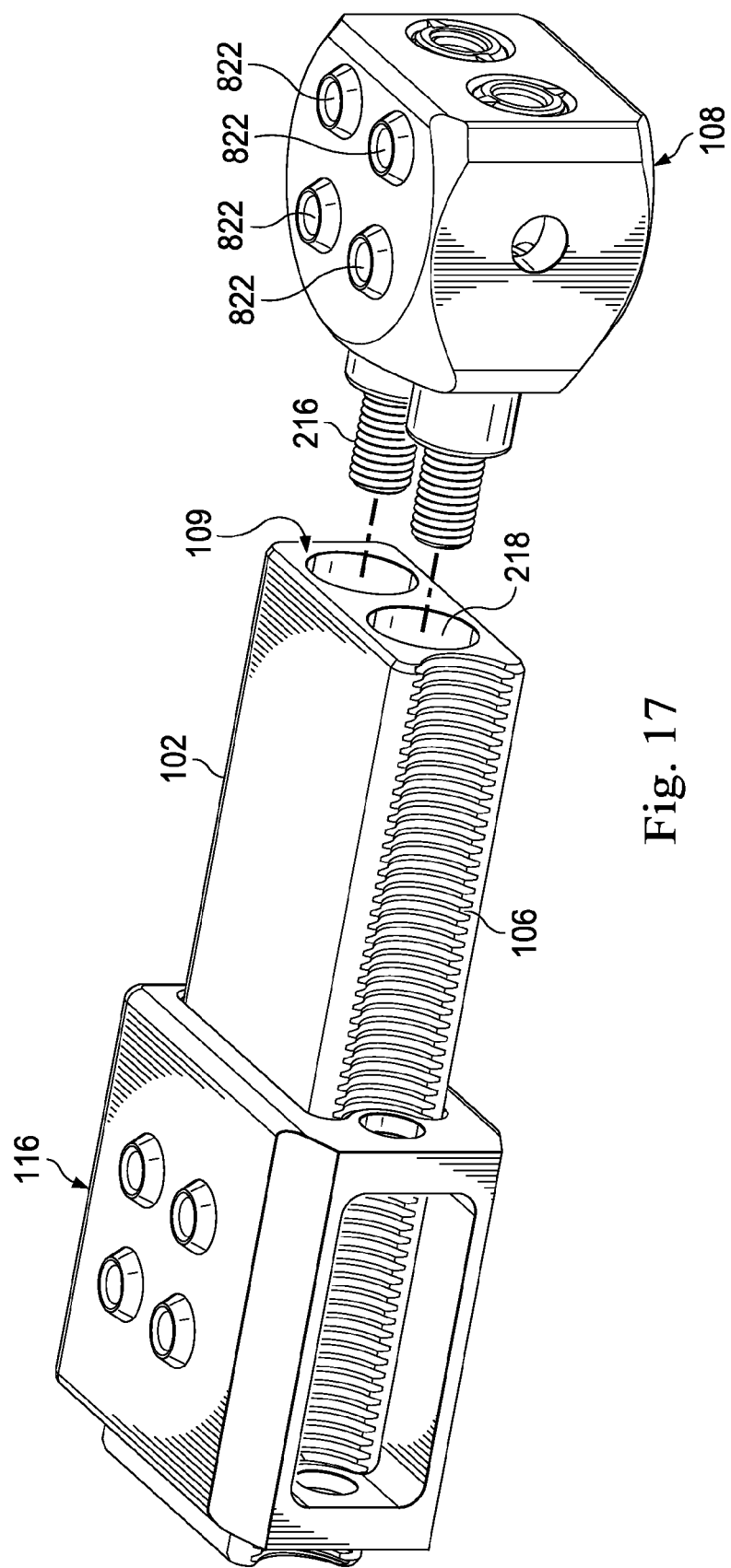
FIG. 17 is a diagram showing a perspective view of a fixed connector element that connects to an end of the beam element according to one example constructed according to principles described herein.

FIG. 17 is a diagram showing a perspective view of a connector element 108 that connects to an end 109 of the beam element 102. According to the present example, instead of a connector element 108 that slides along the elongate beam element 102 and is locked into place, the connector element 108 is configured as an end cap. Thus, the connector element 108 connects to the beam element 102 in a manner similar to the manner in which the supplementary beam element (e.g. 202, FIG. 2) connects to the beam element 102. Accordingly, that connection will not be re-described here.

Figure 18A:
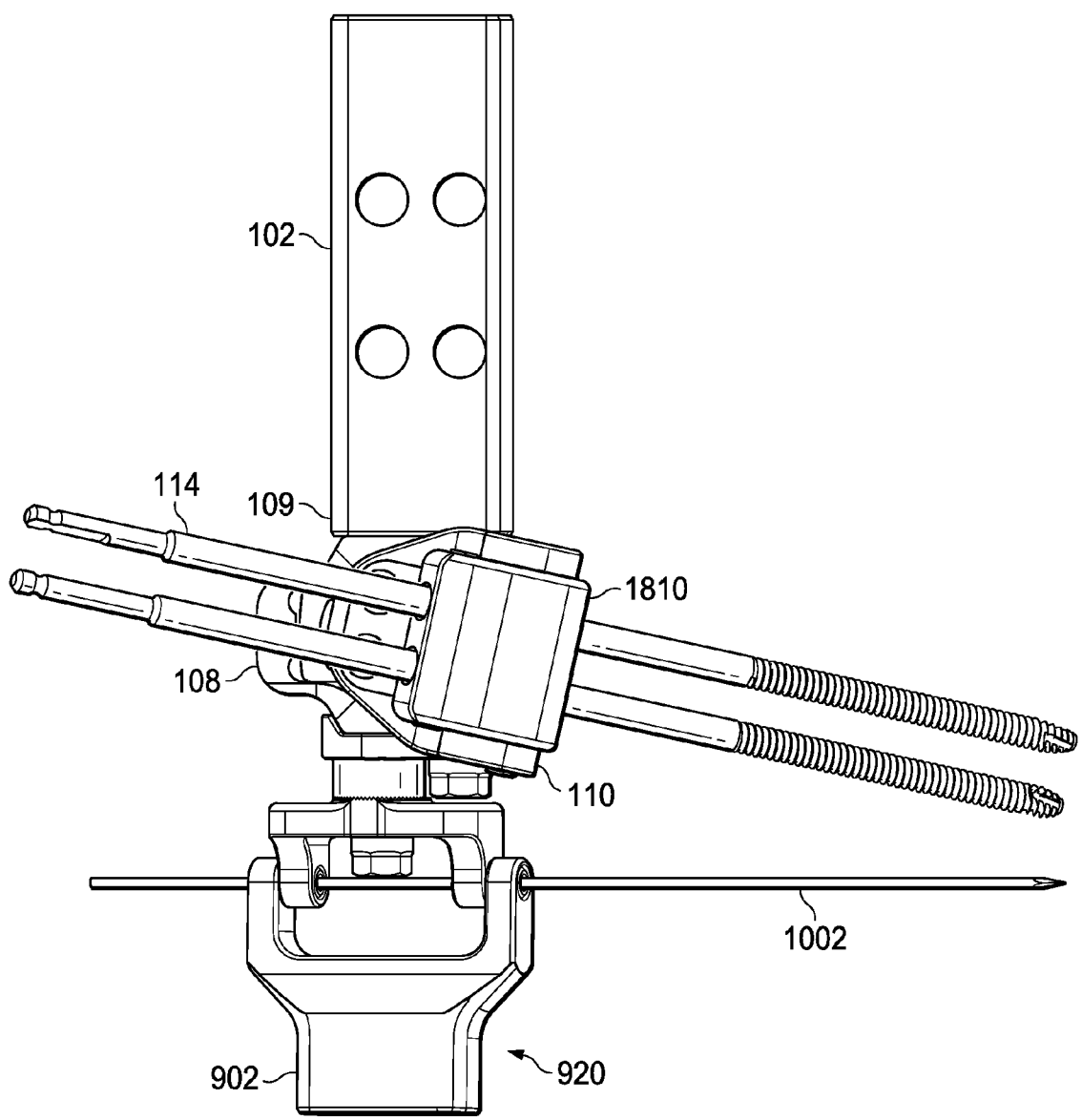
FIGS. 18A and 18B are diagrams showing a hinged anchor block connected to the fixed connector element according to one example constructed according to principles described herein.
Figure 18B:
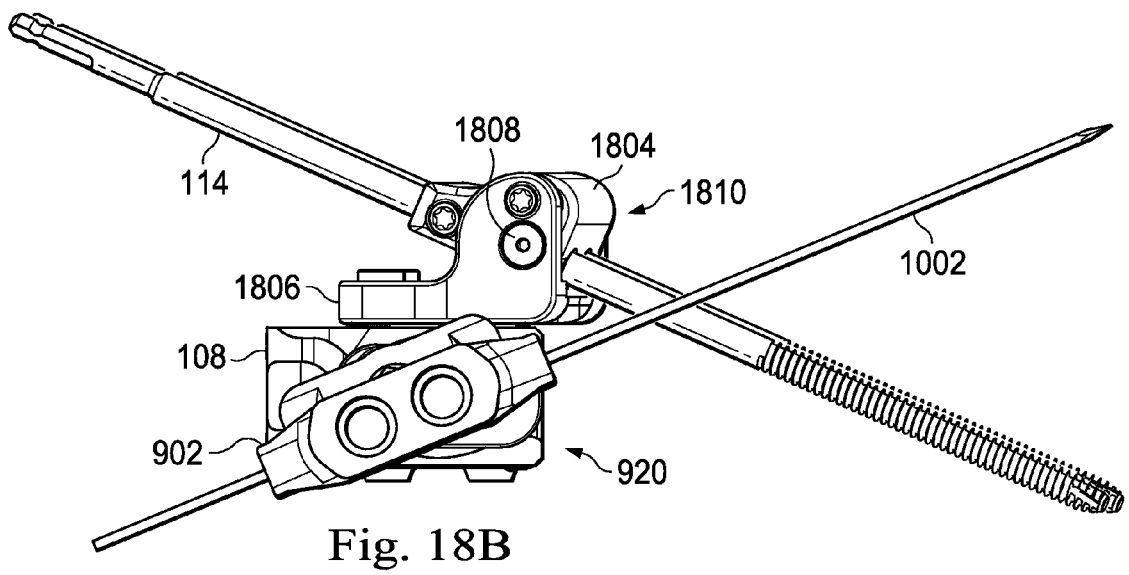

FIGS. 18A and 18B are diagrams showing a hinged anchor block 1810 to connect to the connector element 108. The hinged anchor block 1810 may be similar to the hinge elements described above. FIG. 18A illustrates a top view and FIG. 18B illustrates a side view. According to the present example, the hinged anchor block 1810 includes a first piece 1806 secured to the connector element 108. In some examples, the first piece 1806 can be connected to a turntable (e.g. 803, FIG. 8). The first piece 1806 is connected to a second piece 1804 via a hinge 1808. Thus, the second piece 1804 is rotatable with respect to the first piece 1806 about the hinge 1808. The second piece 1804 holds a set of bone anchors 114. As illustrated in FIG. 18B, the bone anchors 114 may be pivoted about an axis defined by the hinge 1808 with respect to the beam element 102, thus allowing an additional degree of freedom. As can be seen, the connector element 108 is configured with holes 822 that are arranged to connect to the first piece 1806 of the hinged anchor block 1810 in the same manner as it connects to the anchor block (e.g. 110, FIG. 1). Instead of the holes 822, other connection mechanisms are contemplated.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. An external fixation system for the correction of long bone deformities, the system comprising:
   an elongate beam element having an engagement feature along a longitudinal edge of the elongate beam element;
   a connector element secured to the elongate beam and structurally configured to support a first bone anchor extending from the external fixation system; and
   a movable carriage engaged with the engagement feature along the longitudinal edge of the elongate beam element and selectively movable along the engagement feature of the elongate beam element, the movable carriage comprising a rotatable element in engagement with the engagement feature of the elongate beam and also comprising a locking mechanism adjustable between a first setting and a second setting, the first setting allowing the rotatable element to rotate to move the movable carriage along the elongate beam element in only a first direction, and the second setting allowing the rotatable element to rotate to move the moveable carriage along the elongate beam element in only a second direction, the movable carriage being structurally configured to support a second bone anchor extending from the external fixation system.

2. The system of claim 1, further comprising:
   a first anchor block secured to the connector element, the first anchor block being arranged to receive the first bone anchor; and
   a second anchor block secured to the movable carriage and being arranged to receive the second bone anchor.

3. The system of claim 2, wherein the first anchor block is positionable such that the first bone anchor extends in a direction substantially perpendicular to the elongate beam element; and
   wherein the second anchor block is positionable such that the second bone anchor extends in a direction substantially perpendicular to the elongate beam element.

4. The system of claim 2, further comprising, a rotating mechanism that connects the connector element to the first anchor block, the rotating mechanism configured to allow the first anchor block to be set at different angles in relation to the elongate beam element.

5. The system of claim 2, further comprising, a rotating mechanism that connects the movable carriage to the second anchor block, the rotating mechanism configured to allow the second anchor block to be set at different angles in relation to the elongate beam element.

6. The system of claim 1, wherein the engagement feature comprises a set of gear teeth.

7. The system of claim 6, wherein the gear teeth are one of straight and helical.

8. The system of claim 1, wherein the engagement feature comprises partially helical screw threads.

9. The system of claim 1, further comprising a supplementary beam element configured to fixedly attach to an end of the elongate beam element.

10. The system of claim 9, wherein the supplementary beam element has a cross-section perpendicular to a longitudinal axis of the supplementary beam element that is substantially similar to a cross-section perpendicular to a longitudinal axis of the elongate beam element.

11. The system of claim 9, wherein the supplementary beam element comprises an engagement feature that is substantially similar to the engagement feature of the elongate beam element such that the movable carriage can move from a position on the elongate beam element to a position on the supplementary beam element.

12. The system of claim 9, wherein the supplementary beam element comprises an engagement feature that matches the engagement feature of the elongate beam element so as to form a single continuous combined engagement feature along both the elongate beam element and the supplementary beam element.

13. The system of claim 9, wherein the supplementary beam element connects to the elongate beam element through a screw positioned within an internal chamber of the elongate beam element that runs parallel to a longitudinal axis of the elongate beam element.

14. The system of claim 9, wherein the connector element is fixedly attachable to an end of the elongate beam element in a manner similar to a manner in which the supplementary beam element attaches to the elongate beam element.

15. The system of claim 1, wherein the locking mechanism is adjustable to a third setting that prevents rotation of the rotatable element in any direction.

16. The system of claim 1, wherein the locking mechanism comprises a direction indicator indicating a direction of movement of the movable carriage along the elongate beam element.

17. The system of claim 16, wherein the direction indicator is switchable between a) a first position corresponding to the first setting that allows the rotatable element to rotate to move the movable carriage along the elongate beam element in only the first direction, and b) a second position corresponding to the second setting that allows the rotatable element to rotate to move the moveable carriage to move along the elongate beam element in only the second direction, the direction indicator cooperating with the rotatable element such that switching the direction indicator switches the direction of allowable rotation of the rotatable element.

18. The system of claim 16, wherein the direction indicator is arrow-shaped.

19. An external fixation system for the correction of long bone deformities, the system comprising:
a movable carriage structurally configured to support a bone anchor extending from the external fixation system, the movable carriage comprising:
a drive system having a rotatable element engagable with an engagement feature of an elongate beam element in a manner that rotation of the rotatable element advances the movable carriage along the elongate beam element; and
a selectively actuatable lock system structurally arranged to prevent rotation of the rotatable element in at least one direction to prevent advancement of the moveable carriage in at least one direction along the elongate beam element.

20. The system of claim 19, further comprising an anchor block secured to the carriage, the anchor block being arranged to receive and secure the bone anchor.

21. The system of claim 19, further comprising a connector element configured to be secured to the elongate beam element such that the connector element does not move along a length of the elongate beam element.

22. The system of claim 19, wherein the connector element is configured to be secured to an end of the elongate beam element.

23. The system of claim 19, wherein the drive system comprises a gear and the engagement feature comprises teeth.

24. The system of claim 23, wherein the drive system is configured to move the movable carriage along the elongate beam element through rotation of the gear through the teeth.

25. The system of claim 19, wherein the drive system comprises a helical screw and the engagement feature of the elongate beam element comprises helical threads.

26. The system of claim 25, wherein the drive system is configured to move the movable carriage along the elongate beam element by rotation of the helical screw through the helical threads.

27. The system of claim 19, wherein the lock system is configured to selectively also prevent bi-directional rotation of the drive system.

28. The system of claim 27, wherein the lock system is configured to prevent rotation in said at least one direction or prevent bi-directional rotation based on a position of a ratchet mechanism that is biased against a set of teeth formed around an axis of the rotatable element.

29. The system of claim 28, further comprising a spring arranged to bias the ratchet mechanism against the teeth, the spring comprising one of: a helical wire form spring, a monolithic mechanical spring, or an elastomer.

30. The system of claim 28, wherein the ratchet mechanism allows rotation of the rotatable element in only a first direction when in a first position and only a second direction while in a second position.

31. The system of claim 30, wherein the ratchet mechanism prevents rotation of the rotatable element while in a third position.

32. The system of claim 19, wherein the lock system is configured to provide uni-directional rotation of the rotatable element based on a position of a ratchet element that is biased against a set of teeth formed around an axis of the rotatable element.

33. The system of claim 32, wherein the ratchet mechanism allows rotation of the rotatable element in only a first direction when in a first position and only a second direction while in a second position.

34. The system of claim 32, wherein the ratchet mechanism prevents rotation of the rotatable element in both the first and second directions while in a third position.

35. The system of claim 32, wherein the lock system comprises a direction indicator indicating a direction of movement of the movable carriage along the elongate beam element.

36. The system of claim 35, wherein the direction indicator is switchable between a first position that prevents rotation of the gear in the first direction and a second position that prevents rotation of the gear in an opposing second direction, the direction indicator cooperating with the ratchet element such that switching the direction indicator switches the ratchet mechanism.

37. The system of claim 35, wherein the direction indicator is arrow-shaped.

38. An external fixation system usable in the correction of long bone deformities, the system comprising;
an elongate beam element having an engagement feature along a longitudinal edge of the elongate beam element;
a connector element secured to the elongate beam element and structurally configured to support a first bone anchor extending from the external fixation system;
a movable carriage engaged with the engagement feature along the longitudinal edge of the elongate beam element and selectively movable along the engagement feature of the elongate beam element, the movable carriage being selectively lockable into a position along the elongate beam element, the movable carriage being structurally configured to support a second bone anchor extending from the external fixation system;
a rotatable element associated with the moveable carriage and disposed in engagement with the engagement feature of the elongate beam element so that rotation of the rotatable element advances the moveable carriage along the elongate beam element;
a locking mechanism allowing the rotatable element to selectively rotate only in a first direction so that the moveable carriage advances only in a first direction along the elongate beam element; and
a rotating mechanism configured to adjust the bone anchor to different angles in relation to the elongate beam element, the rotating mechanism secured to at least one of: the connector element and the movable carriage.

39. The system of claim 38, wherein the rotating mechanism comprises a turntable.

40. The system of claim 39, wherein the rotating mechanism further comprises a key configured to prevent rotation of the turntable when in a first position and to allow rotation of the turntable in a second position.

41. The system of claim 39, wherein the key is configured to prevent rotation of the turntable through inter-digitation of engagement elements of the key with engagement elements of the turntable.

42. The system of claim 38, wherein the locking mechanism is adjustable between a first setting and a second setting, the first setting allowing the rotatable element to rotate only in the first direction to advance the movable carriage along the elongate beam element in only the first direction, and the second setting allowing the rotatable element to rotate to advance the moveable carriage along the elongate beam element in only a second direction.

43. An external fixation system for the correction of long bone deformities, the system comprising:
   a primary beam element and a selectively attachable secondary beam element, each of the primary and secondary beam elements comprising an engagement feature along a longitudinal edge thereof, the primary and secondary beam elements selectively securable to each other so that the engagement feature of both the primary and secondary beam elements form a continuous engagement feature across the primary and secondary beam elements when secured to each other; and
   a carriage element connectable to the primary and secondary beam elements and comprising a drive system configured to engage with the continuous engagement feature and move the carriage element along the primary and secondary beam elements, the carriage element being structurally configured to support a bone anchor extending from the external fixation system.

44. The system of claim 43, further comprising an anchor block connected to the carriage element and configured to hold a bone anchor.

45. The system of claim 44, wherein the anchor block is reconfigurable with respect to the carriage element such that the bone anchors are angulated relative to a plane of a common interface of the at least one carriage element and the anchor block.

46. The system of claim 45, wherein an amount of angulation relative to the common interface is adjustable.

47. The system of claim 45, wherein the bone anchors are translatable in a plane that is in a fixed orientation relative to the common interface.

48. The system of claim 47, wherein the fixed orientation is parallel to the common interface.

49. The system of claim 44, further comprising a hinge element configured to connect to one of: an end of one of the beam elements or the carriage element.

50. The system of claim 49, wherein the hinge element comprises a movable element that moves within a single degree of freedom about an axis of rotation.

51. An external fixation system usable in the correction of long bone deformities, the system comprising;
   an elongate beam element having an engagement feature associated therewith;
   a connector element secured to the elongate beam element and structurally configured to support a first bone anchor extending from the external fixation system;
   a movable carriage engaged with the engagement feature of the elongate beam element and selectively movable along the engagement feature of the elongate beam element, the movable carriage being selectively lockable into a position along the elongate beam element, the movable carriage being structurally configured to support a second bone anchor extending from the external fixation system;
   a rotatable element associated with the moveable carriage and disposed in engagement with the engagement feature of the elongate beam element so that rotation of the rotatable element advances the moveable carriage along the elongate beam element; and
   a locking mechanism allowing the rotatable element to rotate only in a first direction so that the moveable carriage advances only in a first direction along the elongate beam element.

52. The system of claim 51, wherein the locking mechanism is adjustable between a first setting and a second setting, the first setting allowing the rotatable element to rotate only in the first direction to advance the movable carriage along the elongate beam element in only the first direction, and the second setting allowing the rotatable element to rotate to advance the moveable carriage along the elongate beam element in only a second direction.

53. The system of claim 51, wherein the locking mechanism allowing the rotatable element to rotate only in the first direction is a ratchet element that is biased against teeth formed around an axis of the rotatable element.

54. The system of claim 51, wherein the locking mechanism comprises a direction indicator indicating a direction of movement of the movable carriage along the elongate beam element.

55. The system of claim 54, wherein the direction indicator is switchable between a) a first position allowing the rotatable element to rotate only in a first direction to advance the movable carriage along the elongate beam element in only a first direction and b) a second position allowing the rotatable element to rotate to advance the moveable carriage along the elongate beam element in only a second direction.

56. The system of claim 54, wherein the direction indicator is arrow-shaped.

* * * * *